US012746414B2

(12) United States Patent
Hoey et al.

(10) Patent No.: US 12,746,414 B2
(45) Date of Patent: Sep. 29, 2026

(54) VAPOR THERAPY SYSTEMS AND METHODS

(71) Applicant: FRANCIS MEDICAL, INC., Maple Grove, MN (US)

(72) Inventors: Michael Hoey, Shoreview, MN (US); Roger Noel Hastings, Naples, FL (US); Anthony Christian French, Andover, MN (US); Mark Schrom, Forest Lake, MN (US); Eric Jerke, Dayton, MN (US); Gunnar Askegaard, Maple Grove, MN (US); Chad Naegeli, Maple Grove, MN (US)

(73) Assignee: Francis Medical, Inc., Maple Grove, MN (US)

( * ) Notice: Subject to any disclaimer, the term of this patent is extended or adjusted under 35 U.S.C. 154(b) by 161 days.

(21) Appl. No.: 18/550,886

(22) PCT Filed: Mar. 16, 2022

(86) PCT No.: PCT/US2022/020635
§ 371 (c)(1),
(2) Date: Sep. 15, 2023

(87) PCT Pub. No.: WO2022/197860
PCT Pub. Date: Sep. 22, 2022

(65) Prior Publication Data

US 2024/0189631 A1 Jun. 13, 2024

Related U.S. Application Data

(60) Provisional application No. 63/161,857, filed on Mar. 16, 2021.

(51) Int. Cl.

| | |
|---|---|
| ***A61N 7/02*** | (2006.01) |
| ***A61B 18/04*** | (2006.01) |
| ***A61B 18/08*** | (2006.01) |

(52) U.S. Cl.
CPC ................ *A61N 7/02* (2013.01); *A61B 18/04* (2013.01); *A61B 18/082* (2013.01)

(58) Field of Classification Search
CPC .......... A61N 7/02; A61B 18/04; A61B 18/14; A61B 18/1492; A61B 2018/00547; A61B 2018/048
(Continued)

(56) References Cited

U.S. PATENT DOCUMENTS

| | | | |
|---|---|---|---|
| 408,899 | A | 8/1889 | Small |
| 1,719,750 | A | 7/1929 | Bridge et al. |

(Continued)

FOREIGN PATENT DOCUMENTS

| | | | |
|---|---|---|---|
| CN | 2061443 | U | 9/1990 |
| CN | 2418844 | Y | 2/2001 |

(Continued)

OTHER PUBLICATIONS

US 5,326,343 A, 07/1994, Rudie et al. (withdrawn)

(Continued)

*Primary Examiner* — Beverly M Flanagan
(74) *Attorney, Agent, or Firm* — Shay Glenn LLP

(57) ABSTRACT

A vapor delivery system is provided that may include any of a number of features. One feature of the vapor delivery system is that it can apply condensable vapor energy to tissue, such as a prostrate, to shrink, damage, or denature the prostate. In some embodiments, the vapor delivery system can include safety features including prostate capsule detection, needle tracking, and treatment tracking. Methods for safe and effective treatment of prostate tissues are presented.

18 Claims, 21 Drawing Sheets

(58) Field of Classification Search
USPC .......................................................... 606/27
See application file for complete search history.

(56) References Cited

U.S. PATENT DOCUMENTS

| | | | |
|---|---|---|---|
| 4,672,963 | A | 6/1987 | Barken |
| 4,920,982 | A | 5/1990 | Goldstein |
| 4,950,267 | A | 8/1990 | Ishihara et al. |
| 4,955,882 | A | 9/1990 | Hakky |
| 4,987,781 | A | 1/1991 | Reimann |
| 5,117,482 | A | 5/1992 | Hauber |
| 5,222,185 | A | 6/1993 | McCord, Jr. |
| 5,249,585 | A | 10/1993 | Turner et al. |
| 5,254,096 | A | 10/1993 | Rondelet et al. |
| 5,300,099 | A | 4/1994 | Rudie |
| 5,312,399 | A | 5/1994 | Hakky et al. |
| 5,329,927 | A | 7/1994 | Gardineer et al. |
| 5,330,518 | A | 7/1994 | Neilson et al. |
| 5,341,807 | A | 8/1994 | Nardella |
| 5,353,807 | A | 10/1994 | Demarco |
| 5,366,490 | A | 11/1994 | Edwards et al. |
| 5,370,609 | A | 12/1994 | Drasler et al. |
| 5,370,675 | A | 12/1994 | Edwards et al. |
| 5,370,677 | A | 12/1994 | Rudie et al. |
| 5,385,544 | A | 1/1995 | Edwards et al. |
| 5,409,453 | A | 4/1995 | Lundquist et al. |
| 5,413,588 | A | 5/1995 | Rudie et al. |
| 5,417,701 | A | 5/1995 | Holmes |
| 5,421,819 | A | 6/1995 | Edwards et al. |
| 5,435,805 | A | 7/1995 | Edwards et al. |
| 5,437,660 | A | 8/1995 | Johnson et al. |
| 5,464,437 | A | 11/1995 | Reid et al. |
| 5,470,308 | A | 11/1995 | Edwards et al. |
| 5,470,309 | A | 11/1995 | Edwards et al. |
| 5,484,400 | A | 1/1996 | Edwards et al. |
| 5,499,998 | A | 3/1996 | Meade |
| 5,531,676 | A | 7/1996 | Edwards et al. |
| 5,531,696 | A | 7/1996 | Menes |
| 5,531,763 | A | 7/1996 | Mastri et al. |
| 5,542,915 | A | 8/1996 | Edwards et al. |
| 5,542,916 | A | 8/1996 | Hirsch et al. |
| 5,545,171 | A | 8/1996 | Sharkey et al. |
| 5,549,644 | A | 8/1996 | Lundquist et al. |
| 5,554,110 | A | 9/1996 | Edwards et al. |
| 5,556,377 | A | 9/1996 | Rosen et al. |
| 5,558,673 | A | 9/1996 | Edwards et al. |
| 5,588,960 | A | 12/1996 | Edwards et al. |
| 5,591,125 | A | 1/1997 | Edwards et al. |
| 5,599,294 | A | 2/1997 | Edwards et al. |
| 5,601,591 | A | 2/1997 | Edwards et al. |
| 5,628,770 | A | 5/1997 | Thome et al. |
| 5,630,794 | A | 5/1997 | Lax et al. |
| 5,645,528 | A | 7/1997 | Thome |
| 5,657,760 | A | 8/1997 | Ying et al. |
| 5,667,488 | A | 9/1997 | Lundquist et al. |
| 5,672,153 | A | 9/1997 | Lax et al. |
| 5,681,276 | A | 10/1997 | Lundquist |
| 5,709,680 | A | 1/1998 | Yates et al. |
| 5,720,718 | A | 2/1998 | Rosen et al. |
| 5,720,719 | A | 2/1998 | Edwards et al. |
| 5,776,176 | A | 7/1998 | Rudie |
| 5,792,070 | A | 8/1998 | Kauphusman et al. |
| 5,797,903 | A | 8/1998 | Swanson et al. |
| 5,800,486 | A | 9/1998 | Thome et al. |
| 5,807,395 | A | 9/1998 | Muller et al. |
| 5,810,764 | A | 9/1998 | Eggers et al. |
| 5,830,179 | A | 11/1998 | Mikus et al. |
| 5,843,144 | A | 12/1998 | Rudie et al. |
| 5,849,011 | A | 12/1998 | Jones et al. |
| 5,861,002 | A | 1/1999 | Desai |
| 5,861,021 | A | 1/1999 | Thome et al. |
| 5,871,481 | A | 2/1999 | Kannenberg et al. |
| 5,873,877 | A | 2/1999 | McGaffigan et al. |
| 5,880,486 | A | 3/1999 | Nakamura et al. |
| 5,897,553 | A | 4/1999 | Muller et al. |
| 5,899,932 | A | 5/1999 | Dann et al. |
| 5,928,225 | A | 7/1999 | Falkenstein et al. |
| 5,931,817 | A | 8/1999 | Nguyen et al. |
| 5,938,692 | A | 8/1999 | Rudie |
| 5,944,715 | A | 8/1999 | Goble et al. |
| 5,951,515 | A | 9/1999 | Osterlind |
| 5,957,922 | A | 9/1999 | Imran |
| 5,961,458 | A | 10/1999 | Carroll |
| 5,964,752 | A | 10/1999 | Stone |
| 5,964,756 | A | 10/1999 | McGaffigan et al. |
| 5,976,123 | A | 11/1999 | Baumgardner et al. |
| 5,987,360 | A | 11/1999 | McGrath et al. |
| 5,990,465 | A | 11/1999 | Nakaoka et al. |
| 6,007,571 | A | 12/1999 | Neilson et al. |
| 6,009,351 | A | 12/1999 | Flachman |
| 6,017,358 | A | 1/2000 | Yoon et al. |
| 6,017,361 | A | 1/2000 | Mikus et al. |
| 6,036,631 | A | 3/2000 | McGrath et al. |
| 6,036,713 | A | 3/2000 | Kieturakis |
| 6,053,909 | A | 4/2000 | Shadduck |
| 6,063,081 | A | 5/2000 | Mulier et al. |
| 6,067,475 | A | 5/2000 | Graves et al. |
| 6,077,257 | A | 6/2000 | Edwards et al. |
| 6,113,593 | A | 9/2000 | Tu et al. |
| 6,122,551 | A | 9/2000 | Rudie et al. |
| 6,123,083 | A | 9/2000 | McGrath et al. |
| 6,147,336 | A | 11/2000 | Oshijima et al. |
| 6,148,236 | A | 11/2000 | Dann |
| 6,156,036 | A | 12/2000 | Sussman et al. |
| 6,161,049 | A | 12/2000 | Rudie et al. |
| 6,179,805 | B1 | 1/2001 | Sussman et al. |
| 6,179,836 | B1 | 1/2001 | Eggers et al. |
| 6,206,847 | B1 | 3/2001 | Edwards et al. |
| 6,210,404 | B1 | 4/2001 | Shadduck |
| 6,210,406 | B1 | 4/2001 | Webster |
| 6,223,085 | B1 | 4/2001 | Dann et al. |
| 6,231,591 | B1 | 5/2001 | Desai |
| 6,235,022 | B1 | 5/2001 | Hallock et al. |
| 6,238,389 | B1 | 5/2001 | Paddock et al. |
| 6,238,391 | B1 | 5/2001 | Olsen et al. |
| 6,238,393 | B1 | 5/2001 | Mulier et al. |
| 6,241,702 | B1 | 6/2001 | Lundquist et al. |
| 6,258,087 | B1 | 7/2001 | Edwards et al. |
| 6,272,384 | B1 | 8/2001 | Simon et al. |
| 6,287,297 | B1 | 9/2001 | Woodruff et al. |
| 6,293,792 | B1 | 9/2001 | Hanson |
| 6,302,903 | B1 | 10/2001 | Mulier et al. |
| 6,312,391 | B1 | 11/2001 | Ramadhyani et al. |
| 6,315,777 | B1 | 11/2001 | Comben |
| 6,348,039 | B1 | 2/2002 | Flachman et al. |
| 6,385,472 | B1 | 5/2002 | Hall et al. |
| 6,387,093 | B1 | 5/2002 | Ellman et al. |
| 6,398,759 | B1 | 6/2002 | Sussman et al. |
| 6,409,722 | B1 | 6/2002 | Hoey et al. |
| 6,423,027 | B1 | 7/2002 | Gonon |
| 6,440,127 | B2 | 8/2002 | McGovern et al. |
| 6,461,296 | B1 | 10/2002 | Desai |
| 6,471,637 | B1 | 10/2002 | Green et al. |
| 6,494,902 | B2 | 12/2002 | Hoey et al. |
| 6,496,737 | B2 | 12/2002 | Rudie et al. |
| 6,508,816 | B2 | 1/2003 | Shadduck |
| 6,517,534 | B1 | 2/2003 | McGovern et al. |
| 6,524,270 | B1 | 2/2003 | Bolmsjo et al. |
| 6,537,248 | B2 | 3/2003 | Muller et al. |
| 6,537,272 | B2 | 3/2003 | Christopherson et al. |
| 6,544,211 | B1 | 4/2003 | Andrew et al. |
| 6,551,300 | B1 | 4/2003 | McGaffigan |
| 6,565,561 | B1 | 5/2003 | Goble et al. |
| 6,575,929 | B2 | 6/2003 | Sussman et al. |
| 6,575,968 | B1 | 6/2003 | Eggers et al. |
| 6,579,270 | B2 | 6/2003 | Sussman et al. |
| 6,589,201 | B1 | 7/2003 | Sussman et al. |
| 6,607,529 | B1 | 8/2003 | Jones et al. |
| 6,638,275 | B1 | 10/2003 | McGaffigan et al. |
| 6,640,139 | B1 | 10/2003 | Ueberle |
| 6,669,694 | B2 | 12/2003 | Shadduck |
| 6,676,628 | B2 | 1/2004 | Sussman et al. |
| 6,696,376 | B2 | 2/2004 | Niwa et al. |
| 6,706,039 | B2 | 3/2004 | Muller et al. |

(56) References Cited

U.S. PATENT DOCUMENTS

| | | | |
|---|---|---|---|
| 6,716,252 | B2 | 4/2004 | Lazarovitz et al. |
| 6,719,738 | B2 | 4/2004 | Mehier |
| 6,726,696 | B1 | 4/2004 | Houser et al. |
| 6,730,079 | B2 | 5/2004 | Lovewell |
| 6,736,810 | B2 | 5/2004 | Hoey et al. |
| 6,740,108 | B1 | 5/2004 | Just et al. |
| 6,755,816 | B2 | 6/2004 | Ritter et al. |
| 6,760,616 | B2 | 7/2004 | Hoey et al. |
| 6,780,178 | B2 | 8/2004 | Palanker et al. |
| 6,827,718 | B2 | 12/2004 | Hutchins et al. |
| 6,855,141 | B2 | 2/2005 | Lovewell |
| 6,887,237 | B2 | 5/2005 | McGaffigan |
| 6,890,319 | B1 | 5/2005 | Crocker |
| 6,905,475 | B2 | 6/2005 | Hauschild et al. |
| 6,911,028 | B2 | 6/2005 | Shadduck |
| 6,969,376 | B2 | 11/2005 | Takagi et al. |
| 6,974,455 | B2 | 12/2005 | Garabedian et al. |
| 6,974,968 | B2 | 12/2005 | Houston |
| 7,014,652 | B2 | 3/2006 | Cioanta et al. |
| 7,041,121 | B1 | 5/2006 | Williams et al. |
| 7,066,935 | B2 | 6/2006 | Swoyer et al. |
| 7,089,064 | B2 | 8/2006 | Manker et al. |
| 7,130,697 | B2 | 10/2006 | Chornenky et al. |
| 7,238,182 | B2 | 7/2007 | Swoyer et al. |
| 7,247,155 | B2 | 7/2007 | Hoey et al. |
| 7,261,709 | B2 | 8/2007 | Swoyer et al. |
| 7,261,710 | B2 | 8/2007 | Elmouelhi et al. |
| 7,322,974 | B2 | 1/2008 | Swoyer et al. |
| 7,328,068 | B2 | 2/2008 | Spinelli et al. |
| 7,328,069 | B2 | 2/2008 | Gerber |
| 7,335,197 | B2 | 2/2008 | Sage et al. |
| 7,340,300 | B2 | 3/2008 | Christopherson et al. |
| 7,369,894 | B2 | 5/2008 | Gerber |
| 7,429,262 | B2 | 9/2008 | Woloszko et al. |
| 7,437,194 | B2 | 10/2008 | Skwarek et al. |
| 7,470,228 | B2 | 12/2008 | Connors et al. |
| 7,549,987 | B2 | 6/2009 | Shadduck |
| 7,865,250 | B2 | 1/2011 | Mrva et al. |
| 7,894,913 | B2 | 2/2011 | Boggs et al. |
| 7,959,577 | B2 | 6/2011 | Schmitz et al. |
| 8,048,069 | B2 | 11/2011 | Skwarek et al. |
| 8,216,217 | B2 | 7/2012 | Sharkey et al. |
| 8,244,327 | B2 | 8/2012 | Fichtinger et al. |
| 8,251,985 | B2 | 8/2012 | Hoey et al. |
| 8,272,383 | B2 | 9/2012 | Hoey et al. |
| 8,273,079 | B2 | 9/2012 | Hoey et al. |
| 8,301,264 | B2 | 10/2012 | Achenbach et al. |
| 8,313,485 | B2 | 11/2012 | Shadduck |
| 8,353,818 | B1 | 1/2013 | Sasaki |
| 8,372,065 | B2 | 2/2013 | Hoey et al. |
| 8,388,611 | B2 | 3/2013 | Shadduck et al. |
| 8,409,109 | B2 | 4/2013 | Tiesma et al. |
| 8,419,723 | B2 | 4/2013 | Shadduck et al. |
| 8,470,957 | B2 | 6/2013 | Hikosaka et al. |
| 8,489,172 | B2 | 7/2013 | Gelbert et al. |
| 8,550,743 | B2 | 10/2013 | Bonde et al. |
| 8,585,692 | B2 | 11/2013 | Shadduck et al. |
| 8,632,530 | B2 | 1/2014 | Hoey et al. |
| 8,740,957 | B2 | 6/2014 | Masotti |
| 8,801,702 | B2 | 8/2014 | Hoey et al. |
| 8,900,223 | B2 | 12/2014 | Shadduck |
| 9,198,708 | B2 | 12/2015 | Hoey et al. |
| 9,345,507 | B2 | 5/2016 | Hoey et al. |
| 9,526,555 | B2 | 12/2016 | Hoey et al. |
| 9,833,277 | B2 | 12/2017 | Hoey et al. |
| 9,895,185 | B2 | 2/2018 | Hoey et al. |
| 9,968,395 | B2 | 5/2018 | Hoey et al. |
| 10,194,970 | B2 | 2/2019 | Hastings et al. |
| 10,335,222 | B2 | 7/2019 | Hoey et al. |
| 10,342,593 | B2 | 7/2019 | Hastings et al. |
| 10,390,873 | B2 | 8/2019 | Hoey et al. |
| 10,610,281 | B2 | 4/2020 | Hoey et al. |
| 10,702,327 | B2 | 7/2020 | Hoey et al. |
| 10,751,107 | B2 | 8/2020 | Hoey et al. |
| 10,772,670 | B2 | 9/2020 | Hoey et al. |
| 10,806,502 | B2 | 10/2020 | Hoey et al. |
| 10,987,150 | B2 | 4/2021 | Hoey et al. |
| 11,246,640 | B2 | 2/2022 | Hoey et al. |
| 11,246,641 | B2 | 2/2022 | Hoey et al. |
| 11,246,642 | B2 | 2/2022 | Hastings et al. |
| 11,331,135 | B2 | 5/2022 | Hoey et al. |
| 11,559,345 | B2 | 1/2023 | Hastings et al. |
| 11,564,727 | B2 | 1/2023 | Hoey et al. |
| 11,786,287 | B2 | 10/2023 | Hoey et al. |
| 2001/0032002 | A1 | 10/2001 | McClurken et al. |
| 2001/0037812 | A1 | 11/2001 | Dobak et al. |
| 2001/0047133 | A1 | 11/2001 | Gilboa et al. |
| 2002/0032463 | A1 | 3/2002 | Cruise et al. |
| 2002/0062123 | A1 | 5/2002 | McClurken et al. |
| 2002/0078956 | A1 | 6/2002 | Sharpe et al. |
| 2002/0111617 | A1 | 8/2002 | Cosman et al. |
| 2002/0177846 | A1 | 11/2002 | Mulier et al. |
| 2003/0028172 | A1 | 2/2003 | Epstein et al. |
| 2003/0069575 | A1 | 4/2003 | Chin et al. |
| 2003/0092689 | A1 | 5/2003 | Escandon et al. |
| 2003/0097126 | A1 | 5/2003 | Woloszko et al. |
| 2003/0130575 | A1 | 7/2003 | Desal |
| 2003/0181897 | A1 | 9/2003 | Thomas et al. |
| 2003/0199903 | A1 | 10/2003 | Boesker et al. |
| 2003/0206730 | A1 | 11/2003 | Golan |
| 2003/0216759 | A1 | 11/2003 | Burbank et al. |
| 2004/0006334 | A1 | 1/2004 | Beyar et al. |
| 2004/0039284 | A1 * | 2/2004 | Alam ....................... A61B 8/12 600/439 |
| 2004/0068306 | A1 | 4/2004 | Shadduck |
| 2004/0186422 | A1 | 9/2004 | Rioux et al. |
| 2004/0186468 | A1 | 9/2004 | Edwards |
| 2004/0220462 | A1 | 11/2004 | Schwartz |
| 2004/0225286 | A1 | 11/2004 | Elliot |
| 2004/0230316 | A1 | 11/2004 | Cioanta et al. |
| 2004/0267340 | A1 | 12/2004 | Cioanta et al. |
| 2005/0096629 | A1 | 5/2005 | Gerber et al. |
| 2005/0124915 | A1 | 6/2005 | Eggers et al. |
| 2005/0149020 | A1 | 7/2005 | Jahng |
| 2005/0159676 | A1 | 7/2005 | Taylor et al. |
| 2005/0171522 | A1 | 8/2005 | Christopherson |
| 2005/0273090 | A1 | 12/2005 | Nieman et al. |
| 2006/0089636 | A1 | 4/2006 | Christopherson et al. |
| 2006/0135955 | A1 | 6/2006 | Shadduck |
| 2006/0155210 | A1 | 7/2006 | Beckman et al. |
| 2006/0173242 | A1 | 8/2006 | Novak et al. |
| 2006/0178670 | A1 | 8/2006 | Woloszko et al. |
| 2006/0224154 | A1 | 10/2006 | Shadduck et al. |
| 2006/0224169 | A1 | 10/2006 | Weisenburgh et al. |
| 2006/0253069 | A1 | 11/2006 | Li et al. |
| 2006/0276871 | A1 | 12/2006 | Lamson et al. |
| 2007/0003612 | A1 | 1/2007 | Williams |
| 2007/0027476 | A1 | 2/2007 | Harris et al. |
| 2007/0032785 | A1 | 2/2007 | Diederich et al. |
| 2007/0038039 | A1 | 2/2007 | Adler et al. |
| 2007/0038089 | A1 | 2/2007 | Hatano et al. |
| 2007/0129219 | A1 | 6/2007 | Mahlberg |
| 2007/0142846 | A1 | 6/2007 | Catanese, III et al. |
| 2007/0179491 | A1 | 8/2007 | Kratoska et al. |
| 2007/0179496 | A1 | 8/2007 | Swoyer et al. |
| 2007/0197864 | A1 | 8/2007 | Dejima et al. |
| 2007/0213703 | A1 | 9/2007 | Naam et al. |
| 2007/0293792 | A1 | 12/2007 | Sliwa et al. |
| 2008/0015406 | A1 | 1/2008 | Dlugos et al. |
| 2008/0021484 | A1 | 1/2008 | Catanese, III et al. |
| 2008/0021485 | A1 | 1/2008 | Catanese, III et al. |
| 2008/0033232 | A1 | 2/2008 | Catanese, III et al. |
| 2008/0033458 | A1 | 2/2008 | McLean et al. |
| 2008/0033488 | A1 | 2/2008 | Catanese, III et al. |
| 2008/0039833 | A1 | 2/2008 | Catanese, III et al. |
| 2008/0039872 | A1 | 2/2008 | Catanese, III et al. |
| 2008/0039874 | A1 | 2/2008 | Catanese, III et al. |
| 2008/0039875 | A1 | 2/2008 | Catanese, III et al. |
| 2008/0039876 | A1 | 2/2008 | Catanese, III et al. |
| 2008/0039893 | A1 | 2/2008 | McLean et al. |
| 2008/0039894 | A1 | 2/2008 | Catanese, III et al. |
| 2008/0046045 | A1 | 2/2008 | Yon et al. |
| 2008/0097319 | A1 | 4/2008 | Shih et al. |
| 2008/0110457 | A1 | 5/2008 | Barry et al. |

(56) References Cited

U.S. PATENT DOCUMENTS

2008/0114297 A1 5/2008 Barry et al.
2008/0132826 A1 6/2008 Shadduck et al.
2008/0188811 A1 8/2008 Kim
2008/0208187 A1 8/2008 Bhushan et al.
2008/0208246 A1 8/2008 Livneh
2008/0214956 A1 9/2008 Briggs et al.
2008/0217325 A1 9/2008 Von Buren et al.
2008/0245375 A1 10/2008 Trudel
2008/0249399 A1 10/2008 Appling et al.
2008/0262491 A1 10/2008 Swoyer et al.
2008/0269737 A1 10/2008 Elmouelhi et al.
2008/0269862 A1 10/2008 Elmouelhi et al.
2008/0275440 A1 11/2008 Kratoska et al.
2008/0281297 A1 11/2008 Pesach et al.
2008/0297287 A1 12/2008 Shachar et al.
2008/0312497 A1 12/2008 Elmouelhi et al.
2008/0312521 A1 12/2008 Solomon
2009/0018533 A1 1/2009 Perkins et al.
2009/0018553 A1 1/2009 McLean et al.
2009/0054871 A1 2/2009 Sharkey et al.
2009/0118722 A1 5/2009 Ebbers et al.
2009/0138001 A1 5/2009 Barry et al.
2009/0149846 A1 6/2009 Hoey et al.
2009/0199855 A1 8/2009 Davenport
2009/0216220 A1 8/2009 Hoey et al.
2009/0227998 A1 9/2009 Aljuri et al.
2009/0275971 A1 11/2009 Kelleher et al.
2009/0306640 A1 12/2009 Glaze et al.
2010/0016757 A1 1/2010 Greenburg et al.
2010/0049031 A1 2/2010 Fruland et al.
2010/0054220 A1 3/2010 Bischinger et al.
2010/0069943 A1 3/2010 Roe
2010/0094270 A1 4/2010 Sharma
2010/0114083 A1 5/2010 Sharma
2010/0179416 A1 7/2010 Hoey et al.
2010/0193568 A1 8/2010 Scheib et al.
2010/0204688 A1 8/2010 Hoey et al.
2010/0256636 A1 10/2010 Fernandez et al.
2010/0256679 A1 10/2010 Ducharme
2010/0262133 A1 10/2010 Hoey et al.
2010/0262137 A1 10/2010 Nye et al.
2010/0298948 A1 11/2010 Hoey et al.
2010/0312237 A1 12/2010 Habib et al.
2011/0060328 A1 3/2011 Skwarek et al.
2011/0077628 A1 3/2011 Hoey et al.
2011/0106072 A1 5/2011 Sundquist et al.
2011/0160648 A1 6/2011 Hoey
2011/0264176 A1 10/2011 Jackson et al.
2011/0306950 A1 12/2011 Cucin
2011/0319759 A1 12/2011 Liu et al.
2012/0116392 A1 5/2012 Willard
2012/0197243 A1 8/2012 Sherman et al.
2012/0259271 A1 10/2012 Shadduck et al.
2012/0265186 A1 10/2012 Burger et al.
2012/0265276 A1 10/2012 Curley
2013/0006231 A1 1/2013 Sharma et al.
2013/0066308 A1 3/2013 Landman
2013/0072855 A1 3/2013 Sherry et al.
2013/0074847 A1 3/2013 Hoey et al.
2013/0116683 A1 5/2013 Shadduck et al.
2013/0172867 A1 7/2013 Shadduck et al.
2013/0241320 A1 9/2013 Weinl et al.
2013/0253622 A1 9/2013 Hooven
2013/0261692 A1 10/2013 Cardinal et al.
2014/0039356 A1 2/2014 Sachs et al.
2014/0081208 A1 3/2014 Maloney
2014/0110508 A1 4/2014 Dames et al.
2014/0200568 A1 7/2014 Sharma
2014/0206985 A1 7/2014 Kariv
2014/0276713 A1 9/2014 Hoey et al.
2014/0323837 A1 10/2014 Hirshberg
2014/0354381 A1 12/2014 Kohlhafer
2015/0090762 A1 4/2015 Giordano et al.
2015/0126990 A1 5/2015 Sharma et al.
2015/0157389 A1 6/2015 Ben-Ezra et al.
2015/0272575 A1 10/2015 Leimbach et al.
2016/0008065 A1 1/2016 Gliner et al.
2016/0029960 A1 2/2016 Toth et al.
2016/0081736 A1 3/2016 Hoey et al.
2016/0324575 A1 11/2016 Panescu et al.
2016/0354140 A1 12/2016 Sharma et al.
2017/0196702 A1 7/2017 Agarwat et al.
2017/0231678 A1 8/2017 Sharma
2018/0099124 A1 4/2018 McLoughlin et al.
2018/0168711 A1* 6/2018 Hoey .................... A61B 18/04
2019/0110830 A1 4/2019 Hastings et al.
2020/0197079 A1 6/2020 Fishell et al.
2020/0337756 A1 10/2020 Hoey et al.
2020/0352634 A1 11/2020 To et al.
2020/0397495 A1 12/2020 Hoey et al.
2020/0398032 A1 12/2020 Wang et al.
2021/0052315 A1 2/2021 Rauniyar et al.
2021/0228257 A1 7/2021 Hoey et al.
2022/0096149 A1 3/2022 Sharma et al.
2022/0117648 A1 4/2022 Hastings et al.
2022/0125498 A1 4/2022 Hoey et al.
2022/0125499 A1 4/2022 Hoey et al.
2022/0233228 A1 7/2022 Hoey et al.
2023/0052027 A1 2/2023 Hoey et al.
2023/0052207 A1 2/2023 Hoey et al.
2023/0123218 A1 4/2023 Hastings et al.
2023/0130861 A1 4/2023 Hoey et al.
2023/0414266 A1 12/2023 Hoey et al.
2024/0074805 A1 3/2024 Hoey et al.
2024/0074806 A1 3/2024 Hoey et al.
2024/0081885 A1 3/2024 Hastings et al.
2024/0081886 A1 3/2024 Hoey et al.
2024/0138901 A1 5/2024 Hastings et al.
2024/0407824 A1 12/2024 Hoey et al.
2025/0152226 A1 5/2025 Hoey et al.
2025/0169868 A1 5/2025 Hoey et al.
2025/0169869 A1 5/2025 Hastings et al.
2025/0169870 A1 5/2025 Hoey et al.

FOREIGN PATENT DOCUMENTS

CN 101072544 11/2007
CN 101257855 9/2008
CN 101006939 A 11/2008
CN 101491458 A 7/2009
CN 101554498 A 10/2009
CN 101690834 A 4/2010
CN 101803947 A 8/2010
CN 101854977 A 10/2010
CN 101940482 A 1/2011
CN 20112063 A 6/2011
CN 102338862 A 2/2012
CN 102355864 A 2/2012
CN 102573684 A 7/2012
CN 103796703 A 5/2014
CN 103869269 A 6/2014
CN 104427946 A 3/2015
CN 105873534 A 8/2016
CN 105944188 A 9/2016
CN 106456246 A 2/2017
CN 110177508 A 8/2019
CN 111818862 A 10/2020
EP 0453251 B1 8/1997
EP 2164401 B1 8/2015
EP 2957248 A1 12/2015
JP H0422723 A 1/1992
JP 7-507696 A 8/1995
JP 8-501957 A 3/1996
JP 8-504613 A 5/1996
JP 11-318925 A 11/1999
JP 200014663 A 1/2000
JP 2000005191 A 1/2000
JP 2001500763 A 1/2001
JP 2002035004 A 2/2002
JP 2002515793 A 5/2002
JP 2004065674 A 3/2004
JP 2005502405 A 1/2005
JP 200514085 A 5/2005
JP 2005137916 A 6/2005

(56) References Cited

FOREIGN PATENT DOCUMENTS

| | | | |
|---|---|---|---|
| JP | 2006523116 | A | 10/2006 |
| JP | 2007319691 | A | 12/2007 |
| JP | 2008194072 | A | 8/2008 |
| JP | 2009056176 | A | 3/2009 |
| JP | 4703243 | B2 | 6/2011 |
| JP | 2014521445 | A | 8/2014 |
| JP | 2015502184 | A | 1/2015 |
| JP | 2015096193 | A | 5/2015 |
| JP | 2016515863 | A | 6/2016 |
| JP | 7053741 | B2 | 4/2022 |
| JP | 7366211 | B2 | 10/2023 |
| JP | 7579624 | B2 | 11/2024 |
| WO | WO90/03150 | A1 | 4/1990 |
| WO | WO92/10142 | A1 | 6/1992 |
| WO | WO99/21481 | A2 | 5/1999 |
| WO | WO99/44657 | A1 | 9/1999 |
| WO | WO01/24715 | A1 | 4/2001 |
| WO | WO02/069821 | A1 | 9/2002 |
| WO | WO03/088851 | A1 | 10/2003 |
| WO | WO 03/096871 | A2 | 11/2003 |
| WO | WO2005/102416 | A1 | 11/2005 |
| WO | WO2006/004482 | A1 | 1/2006 |
| WO | WO2007/090074 | A1 | 8/2007 |
| WO | WO2008/083407 | A1 | 7/2008 |
| WO | WO2010/080467 | A2 | 7/2010 |
| WO | WO2012/167213 | A2 | 12/2012 |
| WO | WO2013/160772 | A2 | 10/2013 |
| WO | WO2014/100658 | A1 | 6/2014 |
| WO | WO2016/181384 | A2 | 11/2016 |
| WO | WO99/1481 | A2 | 5/2020 |

OTHER PUBLICATIONS

Envisioneering Medical Technologies; (Screenshot); Targetscan touch: A sterotactic prostate biopsy and treatment system; (http://. envisioneeringmedical.com) product page; 1 page; Available as of Oct. 22, 2008; Acessed from the WayBackMachine on Aug. 20, 2024.

Linmot; Linear motors; 8 pages; retrieved from the internet (https:// linmot.com/products/linear-motors/) on Jan. 31, 2025.

Colin; Focal laser ablation of prostate cancer: definition, needs, and future; Advances in Urology; vol. 2012; Article 589160; DOI10. 1155.2012/589160; 11 pages; Jan. 2012.

Hai; Photoselective Vaporization Prostatectomy: A Palliative Treatment Option for Men with Urinary Obstruction Secondary to Prostate Cancer; PCRI Prost.Cancer Rsrch.Inst. Reprint.from PCRI Insights Nov. 2005, vol. 8(4); Dwnld from http://www.prostate-cancer.org/pcricms/node/233 on May 10, 2012; 4 pages.

Nguyen et al; Updated results of magnetic resonance imaging guided partial prostate brachytherapy for favorable risk prostate cancer: implications for focal therapy; J. Urol.; 188(4); pp. 1151-1156; Oct. 2012.

Hastings et al.; U.S. Appl. No. 19/145,875 entitled “Prostate cancer lesion targeting and vapor needle tip tracking for prostate biopsy and vapr therapy,” filed Jul. 3, 2025.

* cited by examiner

Fig. 2A
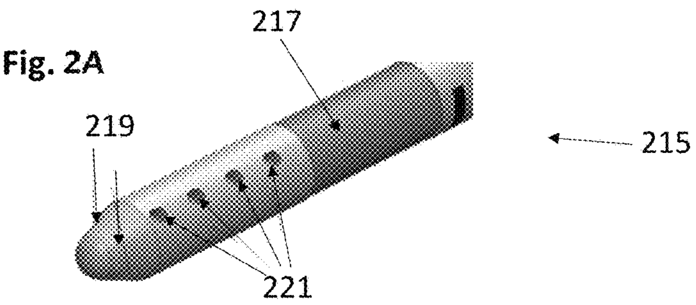
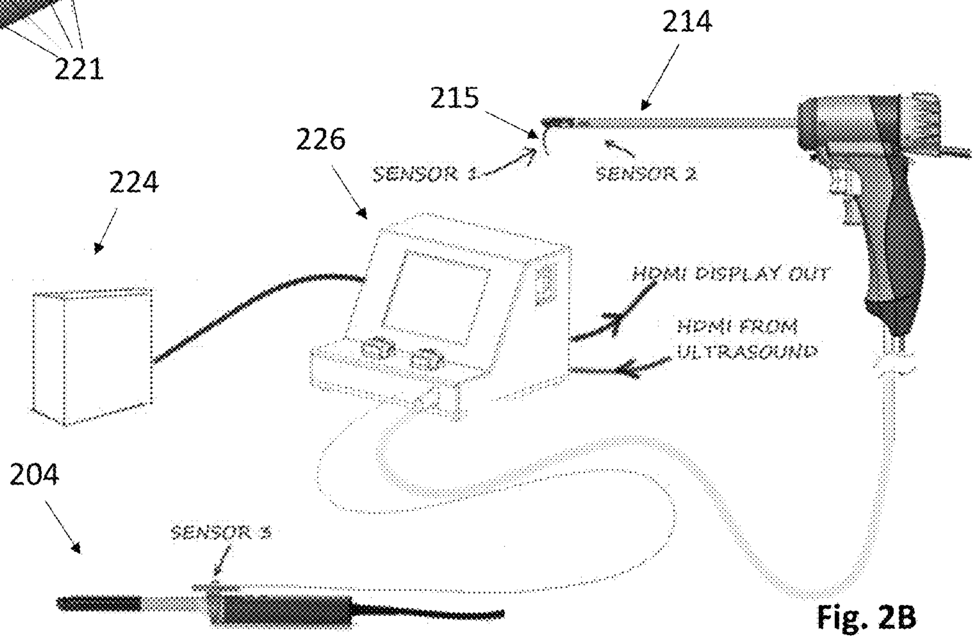
Fig. 2B

FIG. 2G
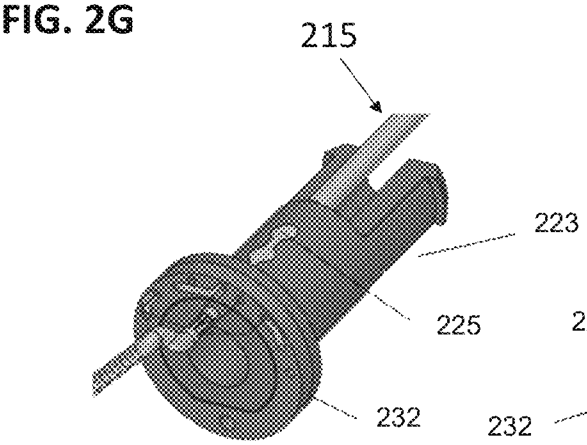
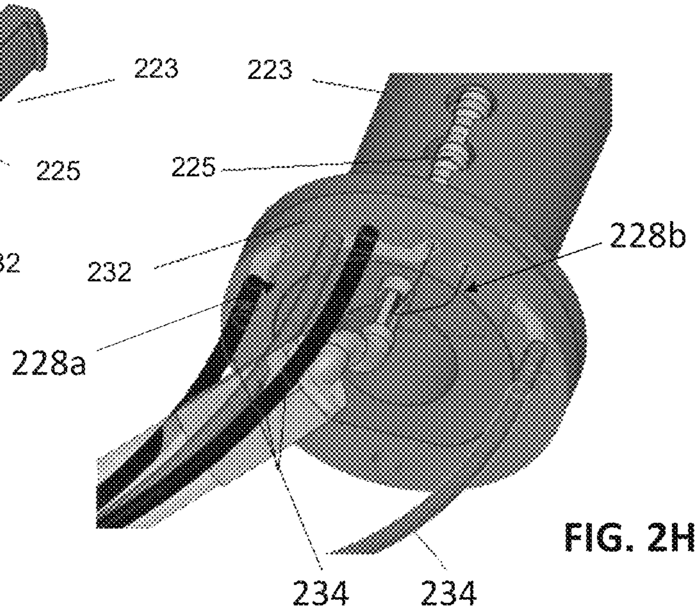
FIG. 2H $R = |Z|/\cos(\phi)$ $C = \sin(\phi)/2\pi f|Z|$ $|Z|$ = impedance magnitude $\phi$ = phase shift between voltage and current FIG. 3A
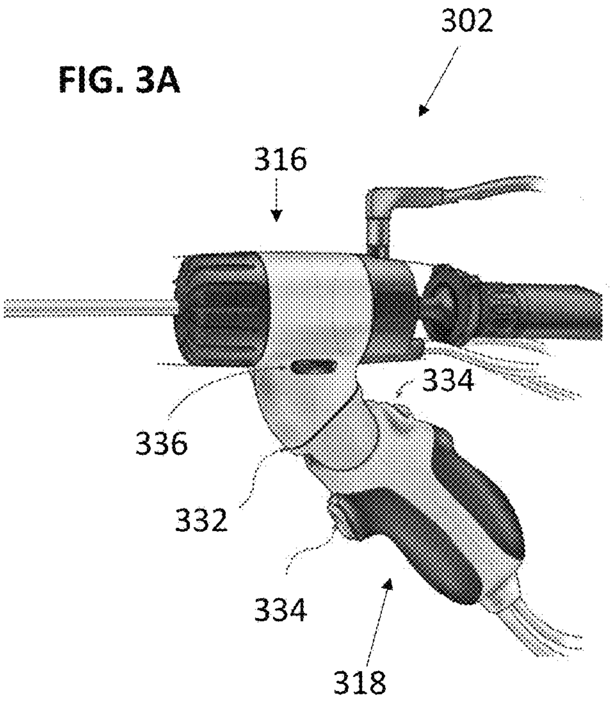
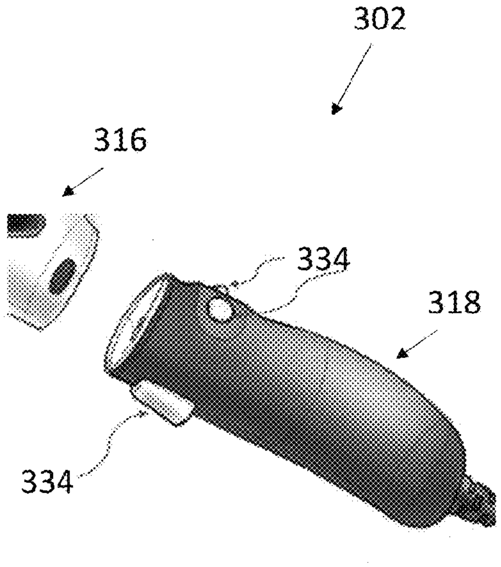
FIG. 3B FIG. 9A
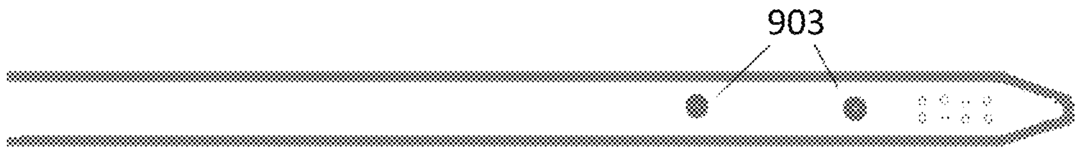
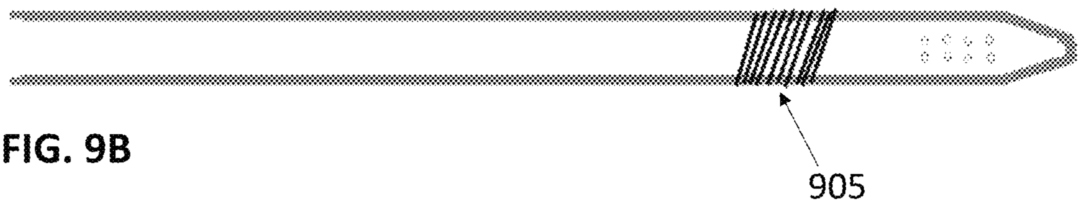
FIG. 9B

VAPOR THERAPY SYSTEMS AND METHODS

PRIORITY CLAIM

This patent application claims priority to U.S. provisional patent application No. 63/161,857, titled "VAPOR THERAPY SYSTEMS AND METHODS" and filed on Mar. 16, 2021, which is herein incorporated by reference in its entirety.

INCORPORATION BY REFERENCE

All publications, including patents and patent applications, mentioned in this specification are herein incorporated by reference in their entirety to the same extent as if each individual publication was specifically and individually indicated to be incorporated by reference.

FIELD

The present invention relates to devices and related methods for treatment of prostate cancer using a minimally invasive approach.

BACKGROUND

The human male prostate can be classified into three zones: the peripheral zone, transition zone, and central zone. Peripheral zone (PZ) comprises about 70% of the volume of a male's prostate. This sub-capsular portion of the posterior aspect of the prostate gland surrounds the distal urethra and 70 to 80% of cancers originate in the peripheral zone tissue. The central zone (CZ) surrounds the ejaculatory ducts and contains about 20-25% of the prostate volume. The central zone is often the site of inflammatory processes. The transition zone (TZ) is the site in which benign prostatic hyperplasia (BPH) develops and contains about 5-10% of the volume of glandular elements in a normal prostate, but can constitute up to 80% of such volume in cases of BPH. The transition zone includes two lateral prostate lobes and the periurethral gland region. There exist natural barriers around the transition zone, i.e., the prostatic urethra, the anterior fibromuscular stroma (FS), and a fibrous plane (FP) between the transition zone and peripheral zone. The anterior fibromuscular stroma (FS) or fibromuscular zone is predominantly fibromuscular tissue.

Approximately 70% to 80% of prostate cancers originate in the peripheral zone of the prostate and may be confined to the peripheral zone. In recent years, there has been an increased interest in focal therapy for prostate cancer, treating only regions of tissue in which cancer has been found following biopsies. Prior art focal therapy treatments, such as with RF ablation energy, may not confine the treatment to the peripheral zone tissue or to tissues within the prostate.

SUMMARY OF THE DISCLOSURE

A prostate treatment system is provided, comprising an introducer shaft sized and configured for transurethral access into a patient, a cartridge coupled to the introducer shaft, a vapor generator disposed in the cartridge and configured to generate a condensable vapor, a handle that is detachably attached to the cartridge, the handle comprising actuators to control vapor delivery functions and may be designed to serve both as a handle during insertion of the introducer shaft into the urethra, and a remote control device when the handle is detached and replaced with an introducer shaft stabilizer device, a needle in communication with the vapor generator and slidably disposed within the introducer shaft, a magnet attached to the needle, a solenoid actuator disposed around the magnet, the solenoid actuator providing controlled movements of the needle to deploy into tissue, advance at constant speed or in pulsed steps, and retract into the shaft, sensors disposed on the needle and shaft, an external Trans Rectal Ultrasound System (TRUS) to provide real time images of the prostate during therapy, a Needle Guidance System (NGS) that converts sensor data to needle tip location and heading within tissue and displays this information on TRUS images, and electronics disposed in the cartridge, handle and an external console that communicate with each other and with the user to ensure safe and effective delivery of vapor to targeted tissues and to prevent delivery of vapor outside of targeted tissues.

In some embodiments, a prostate treatment system is provided, comprising: an imaging system configured to provide real-time images of a patient's prostate; an introducer shaft sized and configured for transurethral access into the patient; a vapor delivery needle slidably disposed within the introducer shaft, the vapor delivery needle being configured to oscillate so as to enhance visibility of the vapor delivery needle in the real-time images from the imaging system; and an advancement mechanism coupled to the therapy needle and configured to advance the vapor delivery needle from the introducer shaft through a prostatic urethra into the patient's prostate.

In some embodiments, the system further includes a magnet coupled to the vapor delivery needle, wherein the advancement mechanism comprises a push pull solenoid driver configured to move the magnet to advance and retract the vapor delivery needle.

In some embodiments, the solenoid driver is configured to oscillate the vapor delivery needle during vapor delivery.

In some embodiments, the system further includes a piezoelectric crystal disposed on or in the introducer shaft, the piezoelectric crystal being electrically coupled to a signal generator and configured to oscillate the vapor delivery needle during vapor delivery.

In another embodiment the system includes a piezoelectric crystal disposed on or in the vapor delivery needle, the piezoelectric crystal being electrically coupled to a signal generator and configured to oscillate the vapor delivery needle during vapor delivery.

In some examples, the system includes a balloon disposed on or in the introducer shaft, the balloon being operatively coupled to a supply lumen, wherein rapid inflation and deflation of the balloon is configured to oscillate the vapor delivery needle during vapor delivery.

In another embodiment, the system includes a balloon disposed on or in the vapor delivery needle, the balloon being operatively coupled to a supply lumen, wherein rapid inflation and deflation of the balloon is configured to oscillate the vapor delivery needle during vapor delivery.

In some examples, the system includes a shape memory foil disposed on or in the introducer shaft, the shape memory foil being electrically coupled to a signal generator and configured to oscillate when current from the signal generator is passed through the shape memory foil to oscillate the vapor delivery needle during vapor delivery.

In one embodiment, the system further includes a shape memory foil disposed on or in the vapor delivery needle, the shape memory foil being electrically coupled to a signal generator and configured to oscillate when current from the signal generator is passed through the shape memory foil to oscillate the vapor delivery needle during vapor delivery.

In some embodiments, the system comprises a solenoid coil disposed on or in the introducer shaft, the solenoid coil being configured to strike the introducer shaft or the vapor delivery needle to oscillate the vapor delivery needle during vapor delivery.

In another embodiment, the system includes a solenoid coil disposed on or in the vapor delivery needle, the solenoid coil being configured to strike the introducer shaft or the vapor delivery needle to oscillate the vapor delivery needle during vapor delivery.

In some embodiments, the imaging system comprises a Doppler ultrasound imaging system.

A method of treating a prostate of a patient is provided, the method comprising: inserting a shaft of a therapy device transurethrally into the patient; advancing a therapy needle from the shaft, through a prostatic urethra of the patient, and into the prostate of the patient; delivering therapy from the therapy needle into the prostate; oscillating the therapy needle; and visualizing the oscillating therapy needle under real-time imaging.

In some embodiments, visualizing the oscillating therapy needle further comprises providing real-time Doppler ultrasound images of the oscillating therapy needle.

In other embodiments, the delivery therapy further comprises delivery vapor therapy from the therapy needle into the prostate.

In some embodiments, advancing the therapy needle from the shaft further comprises actuating a solenoid needle driver that is magnetically coupled to the therapy needle.

In one example, oscillating the therapy needle further comprises oscillating the therapy needle with the solenoid needle driver.

In another embodiment, oscillating the therapy needle further comprises vibrating a piezoelectric crystal disposed on or in the shaft with a signal generator.

In some embodiments, oscillating the therapy needle further comprises vibrating a piezoelectric crystal disposed on or in the therapy needle with a signal generator.

In one example, oscillating the therapy needle further comprises rapidly inflating and deflating a balloon disposed on or in the shaft with a signal generator.

In other embodiments, oscillating the therapy needle further comprises rapidly inflating and deflating a balloon disposed on or in the therapy needle with a signal generator.

In some examples, oscillating the therapy needle further comprises vibrating a shape memory foil disposed on or in the shaft with a signal generator.

In additional embodiments, oscillating the therapy needle further comprises vibrating a shape memory foil disposed on or in the therapy needle with a signal generator.

A prostate treatment device is provided, comprising: an introducer shaft sized and configured for transurethral access into the patient; a vapor delivery needle slidably disposed within the introducer shaft; one or more electrodes disposed on the vapor delivery needle; one or more leads electrically connected to the one or more electrodes and configured to run along a length of the vapor delivery needle; an advancement mechanism coupled to the therapy needle and configured to advance the vapor delivery needle from the introducer shaft through a prostatic urethra into the patient's prostate; and a PCB disposed proximally of the advancement mechanism, the PCB comprising exit holes for the one or more leads and a PCT interconnect configured to electrically couple the one or more leads to a flexible wire lead that extends proximally away from the advancement mechanism.

In some embodiments, the one or more leads include slack between where the one or more leads extend from the exit holes and where the one or more leads connect to the PCT interconnect.

In other embodiments, the slack is provided in the one or more leads due to differential thermal expansion between the one or more wire leads and the vapor delivery needle during vapor delivery.

A prostate treatment device is provided, comprising: an introducer shaft sized and configured for transurethral access into the patient; a vapor delivery needle slidably disposed within the introducer shaft; a device body coupled to the introducer shaft and the vapor delivery needle; and a handle comprising one or more controls for operation of the prostate treatment device, wherein the handle is detachable from the device body and configured to control operation of the prostate treatment device when the handle is attached to the device body and when it is detached from the device body.

In some embodiments, the handle is configured to control vapor delivery.

In another embodiment, the handle is configured to control saline delivery.

In some embodiments, the handle is configured to control vapor delivery needle advancement and retraction.

A surgical therapy system is provided, comprising: a patient table; a horizontal adjustment rail; a first stabilizer arm coupled to the horizontal adjustment rail, the first stabilizer arm comprising an unlocked state in which the first stabilizer arm can be adjusted to any desired bend or position and a locked state in which the bend or position of the first stabilizer arm is locked in place, the first stabilizer arm being adjustable axially along the horizontal adjustment rail relative to the patient table; a second stabilizer arm coupled to the horizontal adjustment rail, the second stabilizer arm comprising an unlocked state in which the second stabilizer arm can be adjusted to any desired bend or position and a locked state in which the bend or position of the second stabilizer arm is locked in place the second stabilizer arm being adjustable axially along the horizontal adjustment rail relative to the patient table; an imaging system coupled to the first stabilizer arm; and a therapy system coupled to the second stabilizer arm.

In some embodiments, the therapy system comprises a vapor therapy system.

In other embodiments, the imaging system comprises a transrectal imaging probe.

BRIEF DESCRIPTION OF THE DRAWINGS

To better understand the invention and to see how it may be carried out in practice, some preferred embodiments are next described, by way of non-limiting examples only, with reference to the accompanying drawings, in which like reference characters denote corresponding features consistently throughout similar embodiments in the attached drawings.

FIG. 21 shows an electrical model of tissue resistance and capacitance.

FIGS. 3A-3D show one embodiment for detaching the vapor delivery device handle from the vapor delivery device cartridge and using the handle as a remote control.

FIGS. 9A-9B illustrate examples of vapor delivery needle tip temperature sensors.

DETAILED DESCRIPTION OF THE INVENTION

Figure 1:
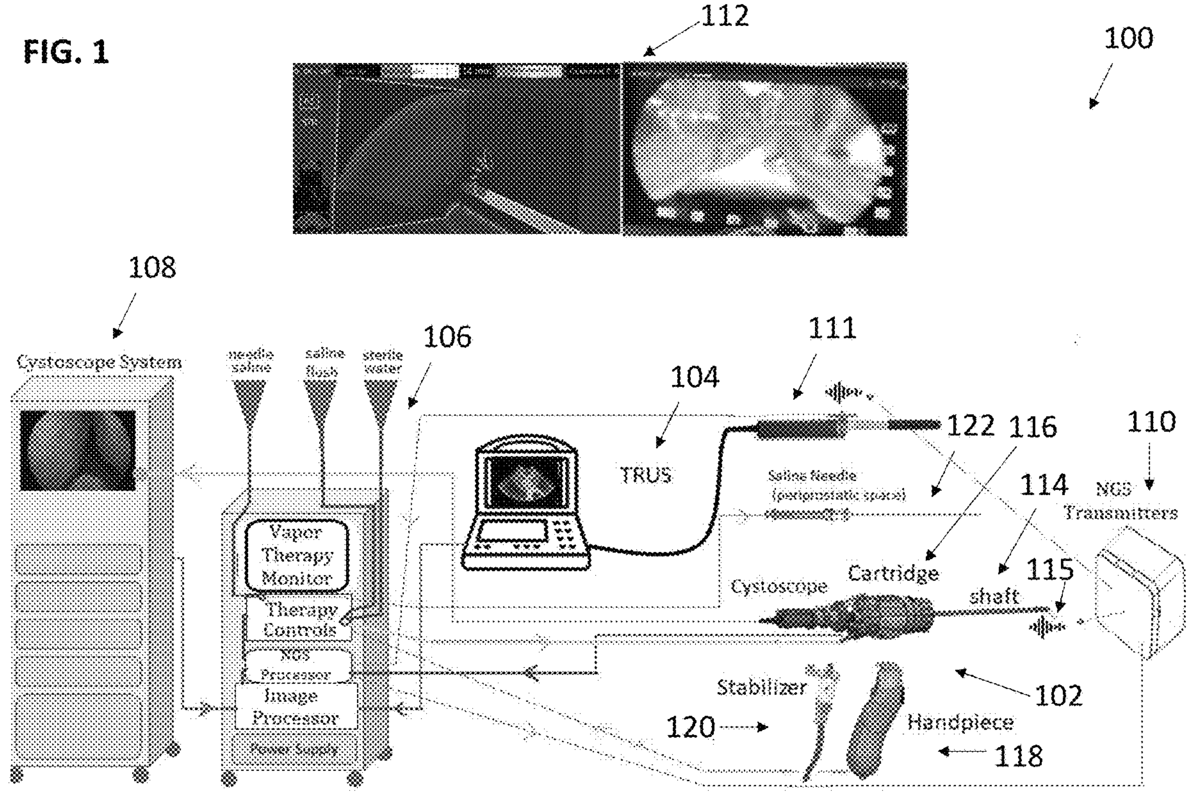
FIG. 1 shows one embodiment of a vapor delivery system.

In general, one method for treating cancer of the prostate comprises introducing a heated vapor interstitially into the interior of a prostate, wherein the vapor controllably ablates prostate tissue. This method can utilize vapor for applied thermal energy of between 50 calories and 600 calories per each individual vapor treatment (and assumes multiple treatments for each prostate lobe) in an outpatient-based procedure. The method can cause localized ablation of prostate tissue without damaging the prostatic urethra and without damaging tissue outside of the prostate gland.

The present disclosure is directed to the treatment of prostate cancer, and more particularly for ablating peripheral zone prostate tissue without ablating central or transitional zone prostate tissue.

The system can include a vapor delivery mechanism that delivers vapor media, including water vapor. The system can utilize a vapor source configured to provide vapor having a temperature of at least 60-140° C. In another embodiment, the system further comprises a computer controller configured to deliver vapor for an interval ranging from 1 second to 30 seconds.

In some embodiments, the system further comprises a source of a pharmacologic agent or other chemical agent or compound for delivery with the vapor. These agents include, without limitation, an anesthetic, an antibiotic or a toxin such as Botox®, or a chemical agent that can treat cancerous tissue cells. The agent also can be a sealant, an adhesive, a glue, a superglue or the like. In some embodiments an echoic or anechoic agent may be delivered with the vapor to improve its visibility under ultrasound imaging to help, for example, in locating the needle tip on the image. Air or other gasses are echoic, for example.

In some embodiments, a prostate treatment device can be provided comprising an introducer shaft sized and configured for transurethral access into a patient, a vapor generator configured to generate a condensable vapor, a vapor delivery needle in communication with the vapor generator and slidably disposed within the introducer shaft, and an actuator configured to move the vapor delivery needle between a retracted position inside the introducer shaft and an extended position at least partially outside of the introducer shaft, and to advance or retract the needle continuously or in steps to tissues at any location between the prostatic urethra and prostate capsule.

This disclosure is directed to safe and effective delivery of vapor to ablate tissue. A vapor delivery device can include a shaft configured for transurethral access to a patient's prostate, a vapor generator, and a vapor delivery needle that can include one or more vapor delivery ports. In one embodiment vapor is delivered through the port(s) of the vapor delivery needle to ablate cancerous or precancerous tissue. In a preferred embodiment, the vapor delivery needle is configured to puncture the prostatic urethra and advance to one or more sites within the prostate where vapor is delivered. Multiple puncture sites can be spaced apart to provide overlapping zones of tissue ablation in the prostate, without being close enough together to allow vapor delivered at a site to exit through the entry holes of the previous puncture sites.

More specifically, this disclosure is directed to navigation of a vapor delivery device, including a vapor delivery needle, into and throughout the prostate to ablate cancerous tissue without the possibility of penetrating the prostate capsule. Vapor is delivered to sites that are surrounded by tissue that has been targeted for ablation. Sensors on the vapor delivery device and on the TRUS (Trans-Rectal Ultrasound System) probe show the operator the location of the needle tip on the TRUS image. Animations superimposed on the ultrasound image can indicate the computed track of the needle tip when it is deployed from a given location in the urethra. With prior art vapor delivery devices, the operator is required to rigidly hold the delivery device in one location as the needle is deployed and advanced to the target site where vapor is delivered. Even small movements of the delivery device can cause delivery of the needle to locations from which the targeted tissue cannot be accessed. Additional needle deployments may be needed to access targeted tissues. Multiple holes through the urethra wall and prostate tissue, especially when closely spaced, may cause vapor to exit through a neighboring hole, thereby under-treating targeted tissues. If the operator moves the delivery device after needle deployment and during navigation to targeted tissues, the track made through tissue may enlarge, causing vapor to exit proximally into the urethra, causing under-treatment of targeted tissues and potential damage to the urethra wall. These concerns are addressed here.

In some embodiments, the vapor delivery device handle can be detached from the device cartridge after the shaft has been advanced into the prostatic urethra. The cartridge can then be attached to a stabilizer arm that is in turn rigidly attached to the patient table. A segmented stabilizer arm may be moved freely until the shaft tip, as observed on the cystoscope and ultrasound images is in a desired location. A motor then activates the stabilizer arm to lock its segments rigidly into place and hold the delivery device cartridge in a desired location. The cartridge and delivery device shaft and needle may be rotated to address tissue in any orientation at that location. The needle may then be deployed through the wall of the urethra and into the prostate, advanced to a desired location where vapor is delivered. The delivery device handle, detached from the cartridge, is used by the operator as a remote control for needle movements and delivery of saline flush and vapor. The stabilizer arm may be unlocked to move the delivery device to new locations in the prostatic urethra, then relocked for vapor delivery to new sites. In some embodiments the stabilizer arm is a robotic arm that is controlled from the system computer.

In other embodiments electrodes are disposed on the needle tip to measure tissue electrical impedance adjacent the tip. Tissue impedance, (both resistance and capacitance) change abruptly as the tissue changes from cellular within the prostate to fibrous in the capsule wall. A coil of fine wire located on the needle tip, just proximal to the vapor delivery holes, comprises a tracking device that locates the needle tip relative to the TRUS image. Fine wire leads from both the impedance electrodes and coil sensor are fed through lumens extruded into the wall of the vapor delivery needle and strain relieved as they exit the proximal end of the needle. Sensor leads exiting the needle are designed to allow for thermal expansion of the needle, and for needle movement during deployment and navigation.

Delivery of vapor to ablate selected regions or zones of the prostate where cancer has been detected can include elevating the temperature of the tissue for a time that is long enough to denature and kill the tissue cells. Temperature sensors on the tip of the vapor delivery needle are disclosed that enable measurement of the temperature of tissues adjacent the needle tip before vapor delivery (to ensure that tissue has not already reached ablation temperature), during vapor delivery (to ensure safe and effective delivery of vapor) and after vapor delivery (to ensure that tissues have reached ablation temperature). In some embodiments the temperature measurement is derived from the electrical resistance of the coil of wire used for needle tip tracking. In one embodiment an AC current is applied to the coil and detected by external magnetic sensors for tracking, while the AC resistance of the coil (voltage amplitude across the coil divided by current amplitude) is simultaneously measured. The coil resistance increases linearly with temperature.

Alternative or additional systems and methods are disclosed for sensing and displaying the location of the needle tip on the TRUS image. In some embodiments the needle tip is vibrated or oscillated with small amplitude that is adequate to detect these movements on the Doppler feature of the TRUS system. When moved, the needle shows up on the TRUS image as blue when the needle is moving toward the TRUS probe, and red when moving away from the TRUS probe. The solenoid needle driver in the device cartridge comprises one means for oscillating the needle with an amplitude and frequency selected by the system or the operator. Other techniques for periodic movements of the needle are disclosed. In some embodiments, a piezoelectric element at the tip of the needle receives the ultrasound signal from the TRUS probe and displays its location on the TRUS image. In other embodiments, a small balloon attached to the delivery needle is inflated through the needle wall lumens with a gas such as air, which shows up brightly on the ultrasound image. As an alternative to a balloon, an echoic fluid or gas may pass through channels in the wall of the needle in pulses and exit near the needle tip. The pulsing fluid will show up on a Doppler mode ultrasound image.

Vapor Delivery System

FIG. 1 shows a vapor delivery system 100 including a vapor delivery device 102, an imaging system 104 such as a trans-rectal ultrasound system (TRUS), a vapor console 106, a cystoscope system 108, a Needle Guidance System (NGS) 110, a saline delivery system 122, and one or more displays 112.

The vapor delivery device 102 can include a shaft 114 that includes a vapor delivery needle 115 configured to be deployed through the wall of the urethra and into prostate tissue. The shaft extends from a vapor delivery device cartridge 116 that is removably attached to a delivery device handle or handpiece 118. In one embodiment, when the handpiece is removed, it can be configured to serve as a remote control for controlling the operation of the vapor delivery device. The vapor delivery device can further include a stabilizer 120 that is flexible and movable but can be activated to a rigid arm that holds and fixes the cartridge relative to the patient. The vapor delivery device can further include a push-pull solenoid needle driver within the cartridge that controls all movements of the needle, and magnetic sensors within the cartridge that monitor the position of the needle driver magnet and therefore the position of the needle relative to the shaft.

The system can further include cables that provide electrical power to the cartridge and relay signals from sensors deployed within the cartridge to measure heating element temperature and needle position within the solenoid, and on the needle and shaft to measure tissue impedance and to measure signals from external tracking antennae, a fluid line that sends sterile water to a vapor generator within the cartridge at a pressure measured within the fluid driver, a fluid line that sends saline flush to cool the shaft during vapor therapy and to clear debris from the view of the cystoscope, and a lumen extending through the cartridge and shaft that removably receives a cystoscope for examination of the urethra and bladder and for monitoring deployment and retraction of the delivery device needle.

Referring still to FIG. 1, the system can further include a vapor delivery console 106 comprising one or more power supplies having capacity to supply the vapor generator, console computers and electronics, and auxiliary equipment such as fluid pumps and tracking system elements. The computers and electronics can be configured to monitor delivery device functions and user commands, condition and process sensor inputs, compute 3D tracks of needle and shaft location and orientation, process ultrasound and cystoscope images, and integrate with animation and tracking software, and communicate with the user of the console. Additionally, the console can include pumping systems configured to create a flow of sterile water, saline flush, and periprostate saline delivery from the console into one or more needles 122. The console can further include sensors for measuring sterile water/vapor line pressure, console internal temperature and electronics currents and voltages. Additionally, the console can include a vapor therapy monitor for displaying real time information on the progress of vapor therapy from the vapor delivery device, including displaying critical sensor outputs and system status. The console can also provide technical information to a user for system monitoring and maintenance.

As described above, the system can be configured to use or coordinate with a cystoscope system 108, which can include instrumentation and one or more displays. The cystoscope system can include a cystoscope configured to be inserted through the vapor delivery device to provide real time images of the urinary tract and the delivery device needle before, during and after needle deployment. In some embodiments, the vapor delivery device can include a lumen in the shaft configured to receive the cystoscope. Displays of the cystoscope system can be configured to display real time cystoscope images to the user during the treatment and therapy. In some embodiments, the cystoscope system can comprise an integrated camera (e.g., miniaturized CMOS sensor(s), for example).

The system can further include a needle guidance system (NGS) 110 which can include many elements. In one embodiment, the NGS can include a transmitter or antenna array configured to generate sinusoidal magnetic fields from one or more array element, and one or more magnetic field sensors integrated onto the needle tip of the vapor delivery device and configured to measure the sinusoidal magnetic fields. The NGS can further include magnetic field sensors mounted on the delivery device shaft tip, and the TRUS probe. Software within the console can be used to convert magnetic sensor data to location and orientation of the needle and shaft tips relative to the TRUS probe. This information can be displayed on the one or more displays 112, including predicted and/or actual tracks of the needle on the TRUS image, marked locations of vapor therapy delivery, predicted zones of ablation on the TRUS image, and TRUS images that are animated and merged with NGS or other data. In some embodiments a magnetic field is transmitted from the needle tip coil and received by an array of magnetic sensors disposed within the TRUS probe.

The system can further include an imaging system 104, which can include, for example a TRUS system. The imaging system can be configured to provide real time images of the prostate gland in one or more views, for example axial and sagittal images. In this embodiment, the imaging system can comprise an imaging rectal probe with integrated NGS sensor(s), a TRUS probe stabilizer, a TRUS image processor and monitor, and controls for selecting image views and parameters.

The one or more displays 112 can be configured to display images of the therapy (such as TRUS images) overlayed with vapor therapy information including NGS tracking information.

Software in the system console 106 combines NGS needle and probe locations and tracks and animations and other information onto the TRUS image. The annotated TRUS image is displayed, along with the cystoscope image, on system monitor(s) 112.

The system can optionally include one or more saline delivery needle(s) 122 which can be used under imaging guidance to inject or apply saline within tissues outside and around the prostate for cooling the peri-prostatic tissues during vapor therap. A layer of saline delivered around the prostate can provide ultrasound contrast to clarify the image of the prostate capsule on a TRUS image.

NGS Tracking System

FIGS. 2A-2B illustrate the components of the needle guidance system (NGS), which can include a field generator 224, a tracking console 226, and one or more sensors placed on the vapor delivery device and/or the imaging system as shown. For example, referring to FIG. 2B, Sensor 1 can be placed on the vapor delivery needle 215, Sensor 2 can be placed on the shaft 214 of the vapor delivery device, and Sensor 3 can be placed on the shaft of the TRUS probe 204. The field generator 224 can comprise an array of coils configured to generate sinusoidal magnetic fields at multiple locations and in multiple orientations. The sensors can then be configured to sense the sinusoidal magnetic fields from the field generator and the console 226 can then be configured to use this data to compute the location (x,y,z) and the polar and azimuth orientation angles (θ,φ) of the sensors relative to the field generator 224, and thereby provide the location and orientation of the needle and shaft tips relative to the TRUS probe 204 and TRUS image(s). The TRUS probe image can then be processed by the vapor delivery console 226 to superimpose the locations of the shaft and needle tip onto the ultrasound image. In some embodiments, an animation can be added that illustrates the shaft, needle tip, potential locations of the needle tip if deployed from the current shaft location along with a cone of uncertainty, the location and extent of previous vapor delivery shots, etc.

FIG. 2A is a closeup view of the vapor delivery needle 215 of the vapor delivery device, illustrating the sensor or NGS tracking coil 217, one or more bio-impedance electrodes 219 (which will be described below), and one or more vapor delivery ports 221.

Figure 2C:
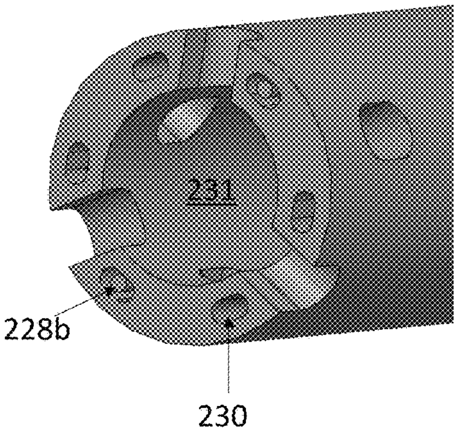
FIGS. 2C-2D show an embodiment of a vapor delivery needle that includes leads from the needle tip through holes in the wall of the delivery device needle.
Figure 2D:
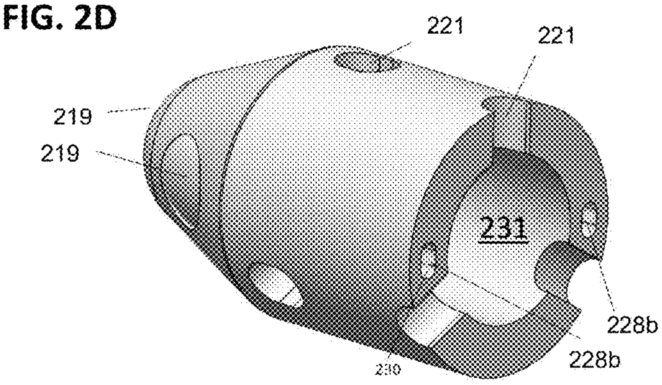
Figure 2E:
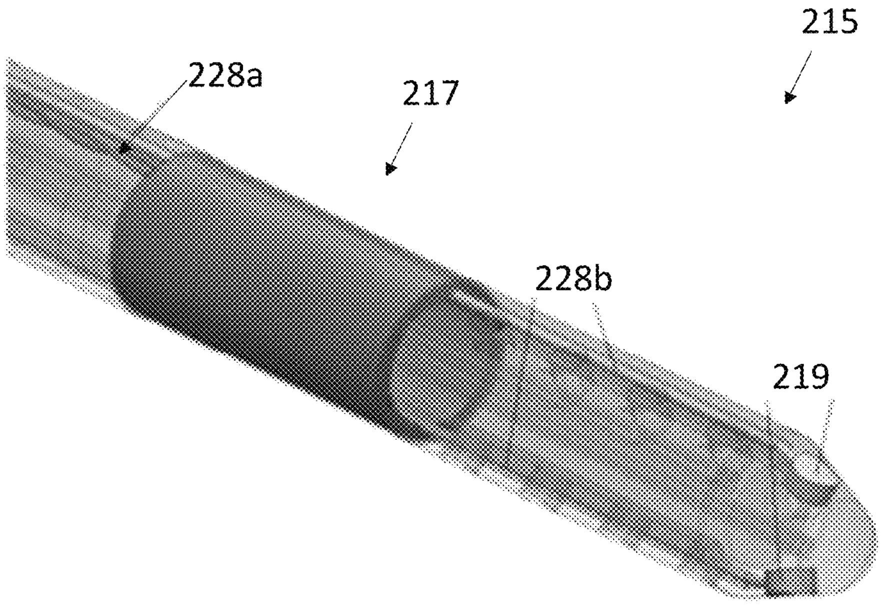
FIG. 2E is one embodiment of a vapor delivery needle including a NGS coil.

The needle tip magnetic sensor 217 may comprise a coil of an insulated fine wire (magnet wire) as shown in FIGS. 2A and 2E. The wire may be wound over a foil of a permeable material such as Alloy 48, and/or the coil may be wound from a magnetically permeable metal such as nickel to enhance sensor sensitivity. Wire gauge in the range of AWG #48-AWG #58 may be used. Finer wire allows more turns of wire in coil 217, wound into a notch cut into the wall of the needle. The voltage induced in the coil or sensor 217 by the field generator is proportional to the number of turns in the coil. However, the signal to noise ratio approaches a constant value for finer wire because the Johnson noise generated in the resistance of the wire is also proportional to the number of turns in the coil for a fixed volume of wire. For heavier wire, the Johnson noise falls below the amplifier noise, which is independent of the coil turns. In one example, coils are wound in a 65 micron deep, 3 mm long slot etched into the wall of a 1.25 mm diameter needle. The signal to noise ratio increases as the wire gets smaller up to #56 gauge. There is no significant improvement in signal to noise ratio going from #56 to #58 wire. #56 wire is chosen for the coil because it is easier to handle than the finer #58 wire.

An example of a coil magnetic sensor 217 wound in a slot near the tip of a vapor delivery needle 215 is shown in FIG. 2E. Leads 228*a* from the coil and leads 228*b* from the bio-impedance electrodes can extend from the needle tip to a proximal end of the needle, where they transition to wires that extend to the vapor console. These leads cannot pass through the vapor delivery lumen 231 without disrupting the flow of vapor. Instead, they are routed through slots 230 extruded into the wall of the needle along its entire length, as shown in FIGS. 2C-2D. Bio-impedance leads 228*b* pass through separate holes, while the leads 228*a* from the coil are twisted together, as shown in FIG. 2E, and pass through a single lumen. In one embodiment, the coil leads are twisted to avoid induction of spurious voltages in spaces between the wires. In some embodiments only two lumens pass through the vapor delivery wall, as shown in FIG. 2D. The two lumens 230 may be used for two bio-impedance leads 228*b* as shown, with no NGS coil. Alternatively, the leads can be used for two twisted pairs comprising leads from an NGS coil and leads for coil voltage measurement for monitoring coil temperature. A cross section of the needle tip is shown in FIG. 2D at the location of the vapor delivery holes 221. The locations and shape of the lumens 230 enables unimpeded clearance for the vapor delivery holes 221.

The bio-impedance electrodes 219 and leads 228*b* are also shown in more detail in FIG. 2E. A constant amplitude sine wave current can be passed between the two bio-cap electrodes. Current flows through the tissue adjacent the needle tip between the tip electrodes. The voltage between electrodes can then be measured. The impedance amplitude is equal to the ratio of voltage and current amplitudes. The phase shift between voltage and current is also measured. An increase in impedance amplitude is seen as the needle tip approaches the prostate capsule. This is due to the less conductive and less capacitive fibrous tissue comprising the capsule, relative to the more conductive and more capacitive cellular tissue within the prostate. Impedance is measured after the vapor delivery needle has been deployed into the prostate. Thereafter, as the needle moves, the ratio of measured impedance to impedance at initial deployment is a preferred alert parameter. The impedance measured after deployment provides a patient specific reference. The ratio may be independent of variations in tissue and environmental factors between patients and procedures.

Figure 2F:
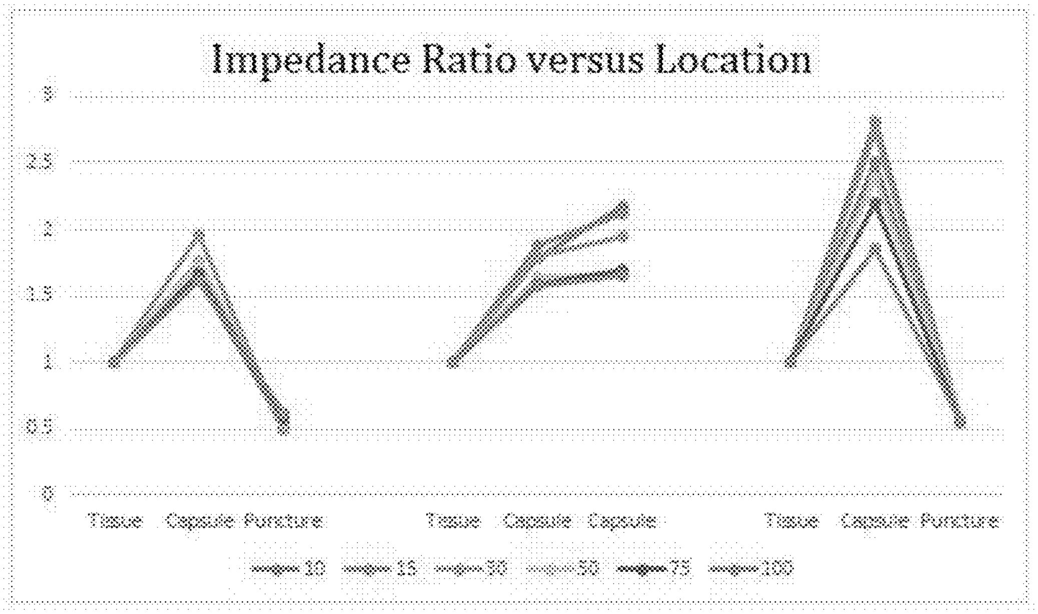
FIG. 2F illustrates a chart that shows a change in bio-impedance measurements when the needle tip contacts the prostate capsule wall versus frequency.

A chart showing the ratio of impedance amplitude at the prostate capsule to impedance amplitude after deployment into prostate tissue (reference impedance) versus frequency, measured in extirpated human prostate, is seen in FIG. 2F. Also shown in FIG. 2F is the ratio of impedance amplitude after the needle has punctured the prostate capsule to initial tissue impedance, versus frequency. It is important to alert the user as the needle approaches the capsule, and even more importantly when the needle has breached the capsule. While vapor therapy may be applied near the capsule, it must not be applied outside the capsule into the peri-prostatic tissues. It was found that the impedance ratios are largest in a preferred range of frequencies between 10 and 50 kHz. Accurate amplitude and phase measurements are made in this range with low-cost electronics, and this range has few environmental noise sources. The frequency that gives the optimal contrast between tissue and capsule (and between capsule and peri-prostatic tissue for detecting capsule puncture) is determined by the size, shape, material, and surface finish of the electrodes and by their separation and locations on the needle tip. Any changes or improvements in these parameters requires new experiments (FIG. 2F) to determine the optimum frequency. One preferred frequency is 15 kHz.

Referring to FIGS. 2G and 2H, a proximal end of the vapor delivery needle 215 is connected to a magnet carrier 223, which is configured to move the needle between a retracted position within the vapor device shaft and a deployed position in which the vapor delivery needle extends out from the shaft. This connection can be with a needle adhesive attachment 225, for example. The previously described leads (such as leads 228*a* and 228*b* above) can exit from holes in a wall of the magnet carrier 223. Here, fine wire leads 228*a* and 228*b* (which are electrically coupled to the bio-impedance electrodes and/or the NGS coils) attach to an interconnect PCB 232 and exit the board as flexible wire leads 234 that enter a cable that plugs into the vapor console. In some embodiments, slack is provided in the fine wire leads 228*b* due to differential thermal expansion between the wire and the vapor delivery needle when vapor is delivered. Slack can also be provided in the flexible wire leads 234 to account for movement of the magnet and needle during needle deploy, retraction and intervening movement.

Figure 2I:
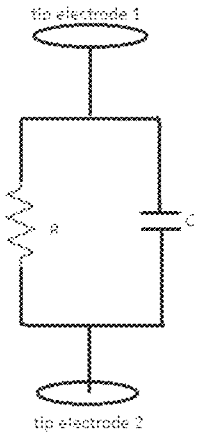
FIGS. 2A-2B illustrate one embodiment of a set of sensors and transmitters that track the locations of the TRUS probe, the vapor delivery needle tip, and the distal end of the vapor delivery device shaft.
FIGS. 2G-2H show one embodiment for strain relief of sensor leads as they exit the vapor delivery needle.

Prostate tissue may be modelled as a resistor in parallel with a capacitor, as shown in FIG. 2I. Resistance and capacitance change as the needle tip enters prostate tissue and approaches the capsule. The values of the tissue resistance and capacitance are derived in terms of impedance magnitude and phase shift between current and voltage via the parallel RC tissue model and the Equations of FIG. 21. The resistance of prostate tissue is lower than the resistance of the fibrous capsule due in part to the lower fluid content of the capsule. The capacitance of the tissue capsule is lower than the capacitance of the prostate tissue due to the acellular fibrous capsule relative to the cellular prostate tissue, where cell membranes contribute to the capacitance. Higher resistance and lower capacitance of the capsule both increase impedance in the parallel model of FIG. 2I, leading to the increase of impedance ratios seen in FIG. 2F. In one implementation, saline can be delivered into tissue surrounding the prostate. The relatively low resistance of saline leads to the drop in impedance as the needle punctures the capsule as seen in FIG. 2F.

Before (in idle mode) and during vapor therapy, condensed sterile water can be continuously ejected from the vapor delivery needle, and there is a possibility that a layer of sterile water may cover the bio-impedance electrodes. Sterile water has very large resistance compared to saline and tissue. However, the capacitance of sterile water is comparable to that of saline and tissue. Therefore, the change in capacitance between tissue and capsule may be more meaningful than the change in resistance or impedance magnitude in the presence of sterile water. In some measurement systems, the value of impedance magnitude $|Z|$ may become high enough in the presence of sterile water to saturate the voltage amplifier, making the computation of R and C less meaningful, while still providing an accurate measurement of phase. This issue may be avoided by measuring the phase shift and reporting $\sin(\varphi)$ as a bio-impedance signal that ranges from zero to one, being zero in purely resistive tissue and one in purely capacitive tissue. In one embodiment the phase angle $\varphi$ itself is reported. The tissue model of FIG. 2I is perhaps the simplest model that accounts for tissue resistance at DC and capacitive coupling at high frequencies. Much more complicated models have been proposed that account for electrical resistance within cells (e.g., adding a resistor in series with the capacitor), non-cellular capacitance in parallel with cell capacitance and resistance, and other nuances. Advanced systems may evaluate the parameters in these models by fitting data taken over a range of frequencies to the model parameters. Tissue models may also account for a layer of charge separation adjacent the electrodes that adds capacitance and resistance that is in addition (in parallel with) tissue capacitance and resistance. This "double layer" contribution to the capacitance approaches zero in pure water. In general, any combination of measured impedance and phase shift and/or computed resistance and capacitance that optimizes the contrast between prostate tissue and prostate capsule, and/or the contrast between prostate capsule and peri-prostatic tissue may be incorporated into the bio-cap system.

In contrast to vapor therapy for BPH where vapor is delivered at a fixed needle depth of 12 mm, prostate cancer therapy requires access to tissues at all depths within the prostate. In preferred embodiments, the vapor delivery needle described herein can access all points on the needle track out to approximately 26 mm. In contrast to one BPH approach of deploy and deliver vapor for 9 seconds, cancer treatment requires deployment followed by slow advancement of the needle to one or multiple sites along the needle track. During navigation and vapor delivery the delivery device must be held fixed at one location. Movements of the needle can enlarge the channel around the needle and cause retrograde expulsion of vapor into the urethra, undertreating at the target site and potentially damaging the urethra lining. This issue may be corrected by delivery of the needle at a nearby location and re-treating. However, if the two insertion holes are close together, vapor delivered at a second site may escape into the urethra through the first needle track. If the physician holding the delivery device moves or rotates the device, even slightly, before deployment, the needle may be deployed to a site from which targeted tissue cannot be accessed. To minimize these issues, the procedure may be performed by two physicians, one holding the delivery device steady while watching the cystoscope image of the needle, and one operating the TRUS system. A simpler procedure requiring only one physician is desired.

FIGS. 3A-3B illustrate one embodiment of a vapor delivery device 302, specifically a controller 318 of the device that can also be used as a detachable handle. Referring to FIGS. 3A-3B, it can be seen how the controller 318 of the vapor delivery device 302 can be detached from the cartridge 316 at detachment point 332. When the controller is detached, it can be used as a remote control with one or more buttons, levers, or controls 334 configured to control operation of the vapor delivery device including the cartridge (e.g., to control vapor/saline delivery, flush, needle advance/retract, and other functions of the device during therapy). It should be noted that both the handle and the cartridge have cables attaching to the console, so that they can communicate with each other when they are detached. Additionally shown in FIG. 3A, the cartridge and/or the controller 318 can further include an attachment point 336 for a detachable stabilizer arm, which will be described in more detail below.

Figure 3C:
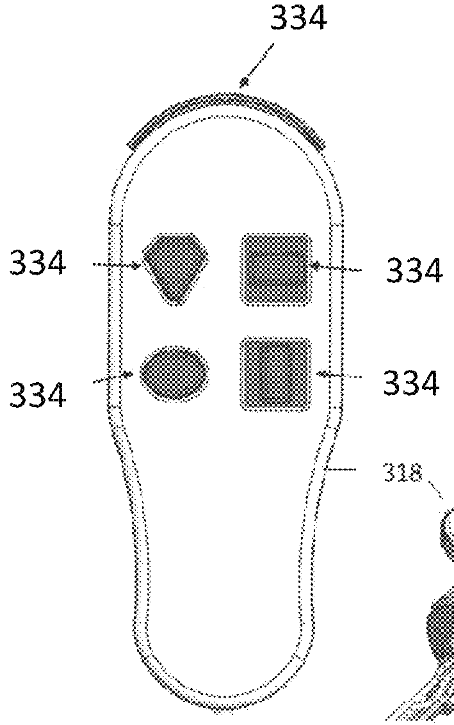
Figure 3D:
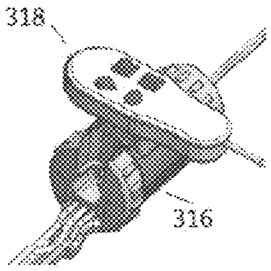

In other embodiments, the controller 318 does not function as a handle for the delivery device. FIG. 3C shows the remote controller 318 separate from the device, and FIG. 3D show a controller 318 removably attached to cartridge 318 while not providing a mechanical handle function. The remote control may be held separately from the cartridge, or it may be used while attached to the delivery device. The remote control includes a plurality of buttons, levers, switches, and/or controls 334 that allow the operator to control advancement or retraction of the vapor delivery needle, therapy ON/OFF, flow of saline coolant through the probe and exiting in the distal urethra, and flow of periprostatic saline flow to tissue around the prostate during therapy. In some embodiments, a toggle switch allows the operator to change ultrasound and camera views of the prostate and delivery device probe. The ultrasound image may be either sagittal or axial views or a combination view, while the cystoscope camera shows the needle injection site. Combination views and image sizes may be selected using the toggle switch.

Figure 4A:
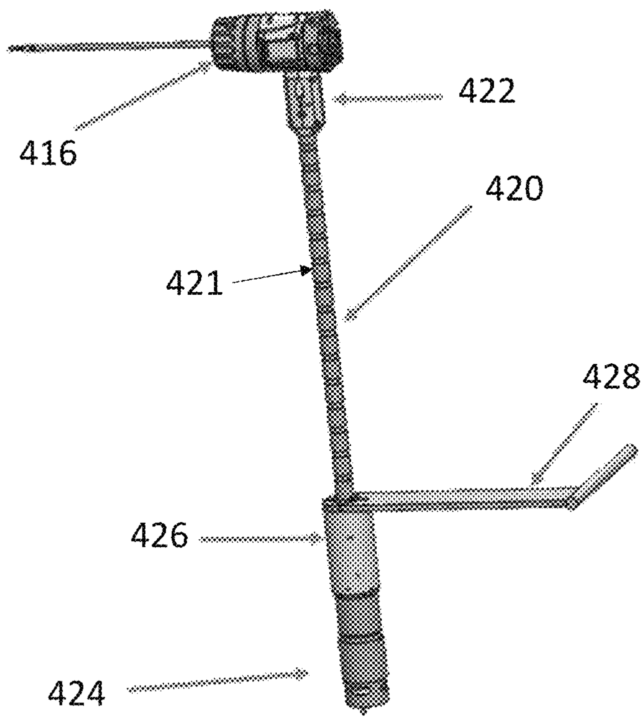
FIGS. 4A-4B illustrate operation of a flexible, lockable arm that allows stabilization of the delivery device and TRUS probe at locations chosen by the user.

A preferred embodiment of this disclosure comprises the stabilizer arm 420 shown in FIG. 4A. The stabilizer arm is configured to be removably attached to the cartridge 416 after the controller described above has been removed or detached from the cartridge. In one example, the stabilizer arm is attached to the cartridge 416 via a coupler 422 that can include locking controls for switching between the stabilizer arm being in a locked state or an unlocked state. The controller then acts as a remote control for vapor therapy functions as described above, while the cartridge 416 is attached to the stabilizer arm 420. The stabilizer arm can further be coupled to a motor 424 with coupler 426. The stabilizer arm comprises a plurality of individual links 421 that have an open end on one side and a rounded "ball joint" end on the other side, configured to interface with the open end of an adjacent link. A DC motor 424 is positioned at a proximal end of the arm, and is coupled to a cable (not shown) which runs through the center of the links and attaches to the distal most link of the stabilizer arm. When the motor/cable is slack, the arm is able to be adjusted to any desired bend or position. Upon activating the motor and tightening the cable, the links are pulled together and locked into place. Control of the motor can be accomplished with controls on the coupler 422, as described above. In use, when the shaft tip reaches a target location within the urethra, the stabilizer motor 424 seen in FIG. 4 is activated by a switch adjacent the top of the stabilizer arm to lock the stabilizer arm segments rigidly together in a three-dimensional arc. The cartridge is then released by the operator and it remains fixed in its desired location and arc relative to the patient table. The operator may unlock and re-position the stabilizer arm. The delivery device shaft may be rotated to a selected angle providing that the needle is retracted.

Figure 4B:
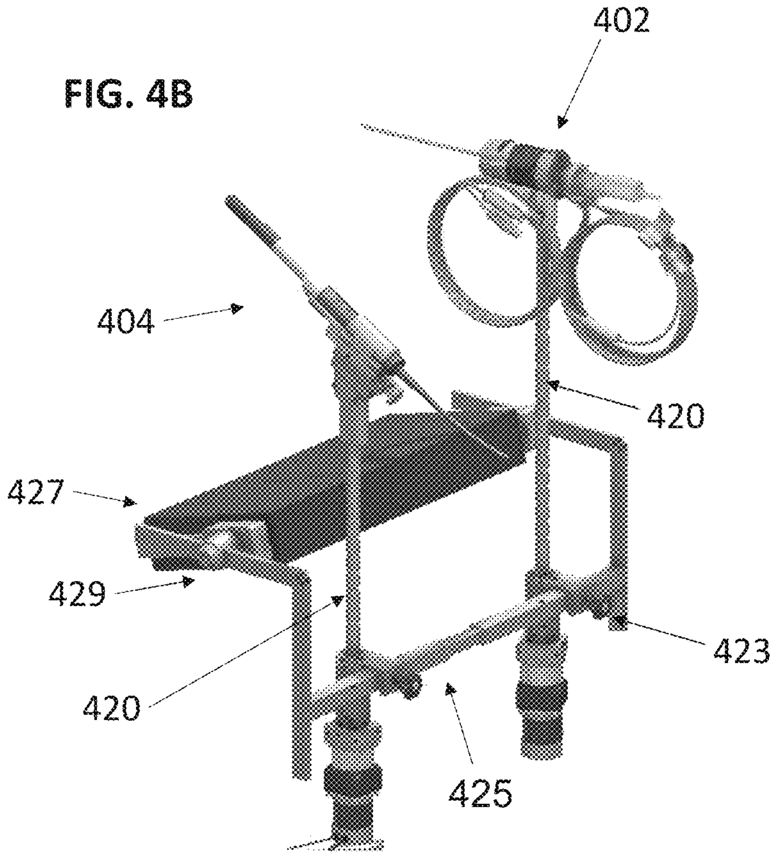

Similarly, referring to FIG. 4B a TRUS probe 404 may be attached to a stabilizer arm in the same manner as the cartridge above. In the embodiment of FIG. 4B, two separate stabilizer arms 420 are used, one for the TRUS probe 404 and another for the cartridge/vapor delivery device 402. Similar to above, the stabilizer arm can be activated and deactivated by a switch at the top of the arm, such as on the coupler between the arm and the probe. Leads from the TRUS probe, and an optional NGS sensor that is rigidly mounted to the TRUS probe, can extend to a TRUS console. The TRUS probe can be set up by manipulating adjustable clamps 423 shown that provide the proper positioning of the probe and stabilizer arm along a horizontal adjustment rail 425 relative to the patient on a patient table 427. As shown, the patient table 427 can also be rotated/adjusted via pivots 429. With the stabilizer arm is deactivated, the TRUS probe is inserted to a desired location in the patient's rectum. The stabilizer arm is then activated to hold the cradle in a fixed location and orientation relative to the patient. The TRUS probe may then be advanced and retracted to adjust the location of the sagittal imaging plane, and rotated to adjust the plane of the axial imaging plane.

Needle deployment, advancement, and vapor delivery then proceeds with little or no disruption of the needle tract, as the cartridge and shaft are held in a stable position by the stabilizer. A single operator may then concentrate on the TRUS images to deliver vapor reliably at target locations without vapor blow-back to the urethra. After delivery of vapor at one or more sites along the needle track, the needle is retracted into the shaft, and the stabilizer arm motor is reactivated to unlock the stabilizer arm segments. The single physician may then manually move the cartridge and shaft to its next location in the urethra and repeat this procedure.

In some embodiments, both the delivery device cartridge and the TRUS probe are attached to motor-controlled stabilizer arms. In some embodiments, a flexible, waterproof sleeve can be placed over the segmented shaft of the two stabilizer arms to protect the arms and prevent water ingress. Electromagnetic tracking sensors (or Needle Guidance System, NGS, sensors) can be rigidly attached to both the delivery device shaft tip and the TRUS probe. The location of the probe tip may thereby be shown on the TRUS image. When the two stabilizer arms are locked into place, the location of the delivery device shaft tip remains stable, even as the delivery device needle is deployed and advanced. The deployed length of needle can be measured in the cartridge by magnetic position sensors that measure the position of the needle advancement magnet relative to its retracted position thereby providing an indication of the needle tip location. With the device stabilized, the needle deploys in a predictable arc. Software can estimate the location of the needle tip post deployment from the needle deployed length measurement and the predicted needle arc, and the estimated location, along with a cone of uncertainty, can be indicated on the TRUS image. The operator may then make small adjustments to the ultrasound imaging plane until the needle shows up clearly in the ultrasound image. As the needle is advanced, the TRUS probe and imaging plane may be advanced or retracted using the TRUS adjustment knob to keep the needle tip in focus. The pair of stabilizers ensures that the TRUS probe and delivery device cartridge do not move relative to each other during needle movements. Prior art TRUS stabilizers are large and cumbersome. The motorized locking arm described herein provides a low profile, simple to use stabilizer.

Figure 5A:
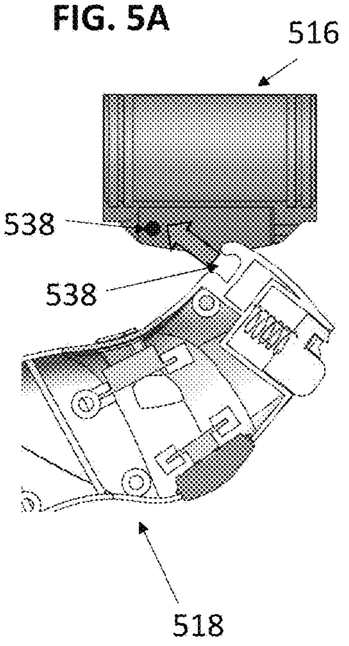
FIGS. 5A-5C show one embodiment for a detachable handle of a vapor delivery device.
Figure 5B:
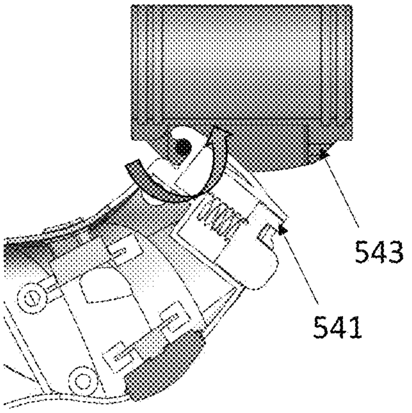
Figure 5C:
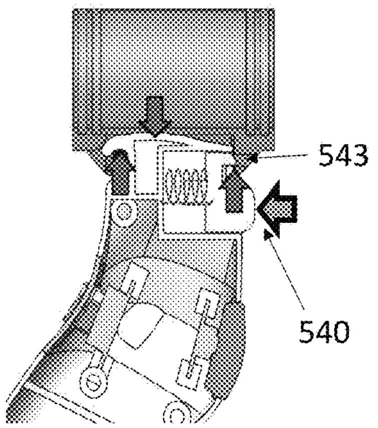

A simple and ergonomic system for attaching and removing a delivery device handle or controller 518 from the cartridge 516 is shown in FIGS. 5A-5C. As shown, the handle or controller can be attached to the cartridge by clipping an engagement feature 519 of the cartridge into a notch 538 on the handle, swinging the handle up, and pushing the handle until it clicks into place within the cartridge. As shown, the handle or controller can include a spring-loaded actuator 540. When the handle is clicked into place, an arm 541 of the actuator fits into a slot 543 in the cartridge. The handle is released by pushing in the spring-loaded actuator 540, removing the handle and replacing it with the stabilizer arm.

Figure 6A:
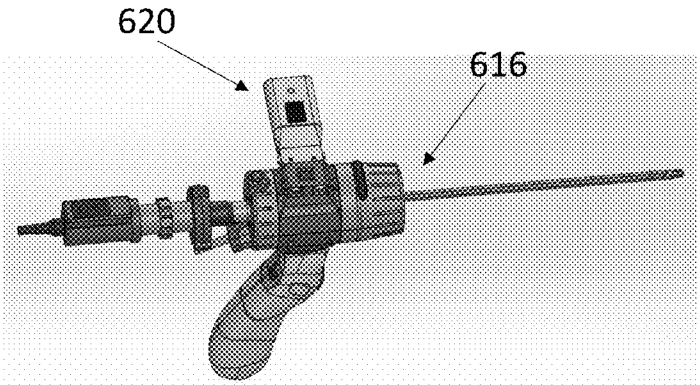
FIGS. 6A-6B show how the stabilizer arm attaches to the cartridge of the vapor delivery device.
Figure 6B:
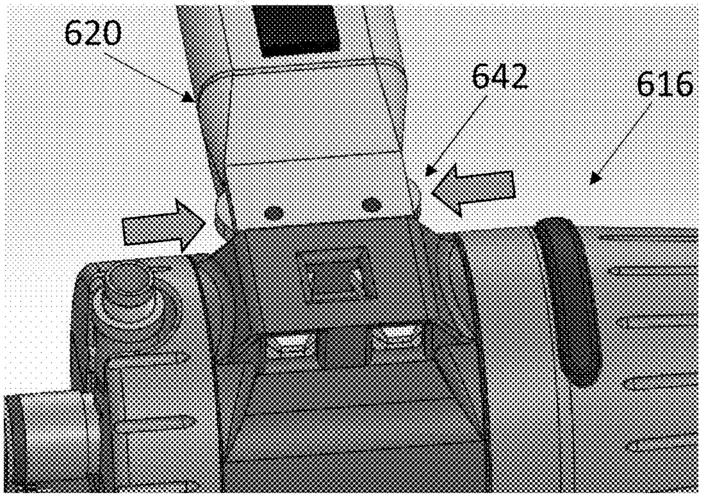

Referring to FIGS. 6A-6B, a similar mechanism can be used to attach the stabilizer arm 620 to the cartridge 616 of the vapor delivery device. For example, one or more notches or complimentary engagement portions can be used to connect the two components. In one embodiment, they can be held in place with one or more spring loaded actuators 642. The stabilizer can click or lock into place when the two are connected. Pressing in the actuators 642 can release the stabilizer from the cartridge. In the illustrated embodiment, the stabilizer can be attached to the cartridge even when the handle is still attached to the cartridge. In another embodiment, it is contemplated that the stabilizer is attached to the cartridge at the same place where the handle attaches to the cartridge (therefore requiring the handle to be removed prior to attaching the stabilizer).

Prior art vapor delivery devices have employed rf current flowing though a coil that inductively couples to a heating element tube through which sterile water is pumped to create steam. Ohmic heat generated in the rf coil contributes little to heating water flowing through the induction coil, while adding substantial heat to the delivery device and elevating its temperature. In this disclosure, DC current is passed directly through a heating element tube 744 via specially designed high current connectors 746 electrically connected to a PCB 748 seen in FIGS. 7A-7B. As shown, the high current connectors 746 can include a cutout our notch designed and configured to cradle or hold the heating element tube 744. In this example, two high current connectors 746 hold and support the entire tube 744, a first connector holding an inlet portion of the tube that extends axially along a length of the vapor delivery device, and the second high current connector holding a coiled portion of the tube that extends generally radially or orthogonally relative to the inlet portion. DC current can be supplied from a 24 Volt, 0-25 Amp medical grade DC power supply located in the system console. Voltage across the heating element, and current through the heating element can then be measured and multiplied to provide an accurate, real-time measurement of power being dissipated in the heating element. Heating element power can be servo controlled to a set power by a Pulse Width Modulation (PWM) circuit in the console. The calorie per second vapor output of the system is proportional to the heating element power through an efficiency factor. Controlling the heating element power controls caloric output independent of any changes in the heating element electrical load. In contrast to rf heating elements, the temperature of the cartridge wall surrounding the DC heating element is always low enough to be comfortably gripped by the operator.

Figure 7A:
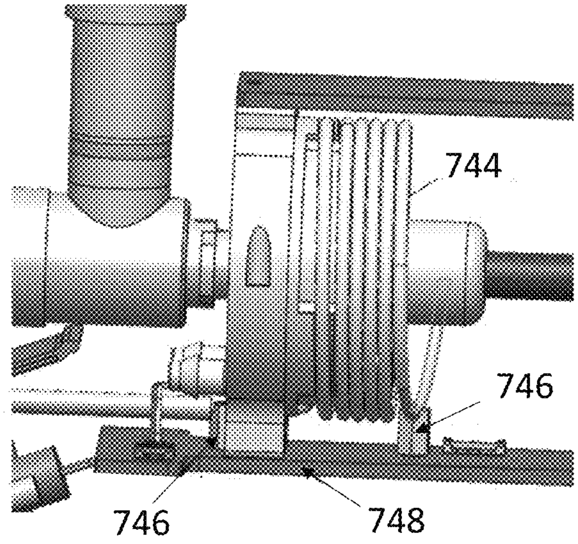
FIGS. 7A-7C illustrate one embodiment of a vapor generator coil including a technique for mounting the vapor generator coil to a printed circuit board.
Figure 7B:
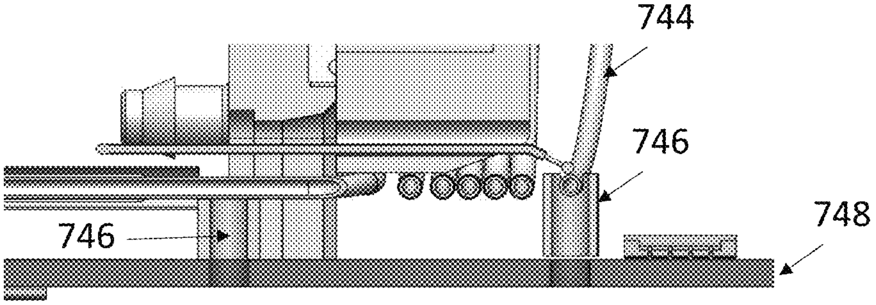

The heating element of FIGS. 7A-7B can be constructed from Inconel 625 stainless steel, chosen for its relatively high electrical resistivity, and especially because its electrical resistance is nearly independent of temperature over its operating range, nominally 20-300° C. Since room temperature sterile water enters the heating element 744 and water vapor exits the heating element at a temperature greater than 100° C., there exists a temperature gradient along the tube. If the electrical resistance of the heating element tube increased with temperature, the distal end of the tube would have a higher resistance and more Ohmic $I^2R$ heat would be dissipated at the distal end of the tube, leading to less efficient conversion to vapor and excessively high vapor outlet temperatures. The Inconel 625 can be covered by a thin-wall polyimide tube having excellent electrical insulating properties and high temperature stability. The windings of the insulated heating element can be pre-stressed to force the windings into good thermal contact. This reduces the temperature gradient along the tube and leads to more efficient vapor generation. Elevated temperatures in the heating element allow more heat to escape to the delivery device cartridge via conduction, convection, and radiation. Hot spots on the cartridge can be a safety concern. Higher efficiency (lower heat loss) translates to more consistent vapor caloric output. For these reasons, minimization of heat loss from the heating element is important.

In the design of FIGS. 7A-7B, conductive heat loss is minimized by having mechanical attachment at the cool input end of the heating element with only an electrical connector contacting the heating element at the hot or distal end. A brass, stainless steel, or Inconel high current connector 746 can be welded or mechanically attached to the heating element and soldered to thick, low resistance traces on a PCB (Printed Circuit Board) 748. The traces provide mechanical stability and a very low electrical resistance connection. The PCB provides a landing for other electrical leads in the system as they exit through the delivery device cable. A thermocouple can be welded to the distal end of the heating element to monitor vapor exit temperature and can be used by the console to shut down the system if the temperature is outside a prescribed range. In some embodiments, the thermocouple is welded distal of the electrical connector. This is because DC current flowing along the length of the heating element tube creates an IR voltage drop across any thermocouple placed proximal to the distal connector post. The thermocouple cannot distinguish an IR voltage drop from the drop across the dissimilar metals comprising the thermocouple. If the thermocouple is welded proximal of the distal connector, a stray voltage will appear at the thermocouple junction and be interpreted in software as a false temperature reading. The stray voltage will depend upon the distribution of materials in the thermocouple weld ball, so will be different for all devices. There is no current flow and no stray voltages distal to the distal connector.

In some embodiments the thermocouple can be positioned proximal to the distal connector, for example for fast detection of an air bubble that may greatly reduce convective cooling of the tube. Current flowing through the tube at the site of the air bubble will rapidly heat the tube at that site, an event that will be detected by a thermocouple placed proximal of the distal connector. IR drop errors in the thermocouple reading may be reduced by attaching the two thermocouple leads to the tube circumferentially around the tube, so they are at the same electrical potential. A thin layer of electrically insulating material may be placed between the thermocouple and the heating element tube to insulate the weld ball from the heating element. An alternative technology thermometer, for example an RTD (resistance thermometer) may be employed which is not impacted by current flowing through the heating element tube. In one embodiment insulated fine wire is wound around the tube forming a coil. The resistance of the coil is monitored. For coil wire materials such as copper or platinum, the coil resistance increases linearly with temperature over the operating temperature range (20° C.-300° C.). The coil may be made non-inductive (to prevent induced noise voltages) by doubling a length of wire back on itself before winding. RTDs are generally more accurate and robust than thermocouples, and easier to connect to external electronics. Other thermometer types that may be used in this application include thermistors and chip mounted optical thermometers. In some embodiments micro-thermometers may be placed at two or more locations along the length of the heating element tube.

A sensor may be configured to measure pressure in the sterile water delivered to heating element 744. Water pressure is impacted by the generation of vapor in heating element 744. Measurable changes in pressure occur, for example, when an air bubble passes through the heating element creating both pressure and temperature spikes. Power to the heating element can be automatically shut down when water pressure exceeds a preset value for a preset time.

Figure 7C:
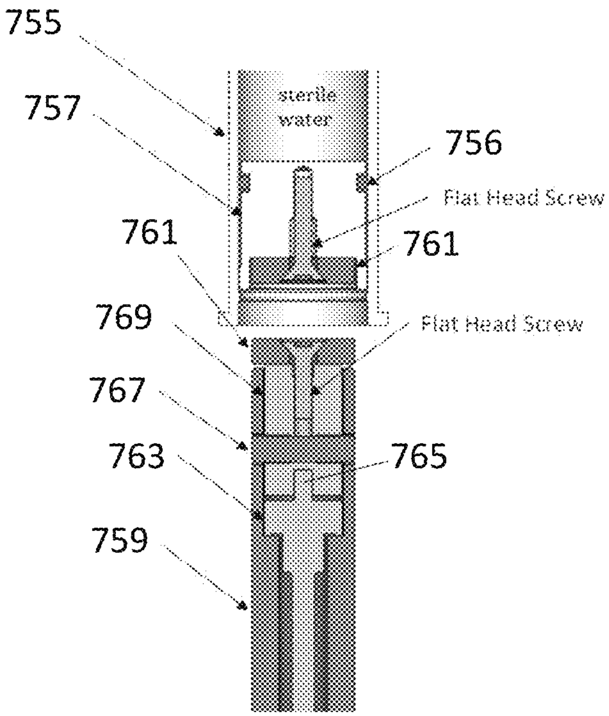

In one preferred embodiment, shown in FIG. 7C sterile water is pushed by a syringe 755 through the delivery system water line and into heating element tube 744. The syringe plunger 757 can be advanced and retracted by a stepper motor (not shown) that advances/retracts the plunger shaft 759. An O-ring 756 can be provided between the plunger and the syringe. The plunger and plunger shaft can be coupled via magnets 761, enabling detachment of the disposable syringe from the console plunger shaft 759. As the plunger shaft is advanced, force is applied to the plunger 757 through the load cell 763 and load cell button 765. The pressure can then be calculated as the measured force between the load cell and load cell button divided by the cross-sectional area of the plunger. In one example, this load cell button moves a total of 18 microns relative to the load cell as the force increases from zero to 50 pounds. A clearance of 0.5 mm between a dowel pin 767 and load cell adaptor 769 allows ample clearance for the small displacement of the load cell button. Leads from the load cell exit the proximal plunger shaft to the console electronics. The load cell measures pressure and changes in pressure throughout the sterile water line, including the heading element tubing and the vapor delivery needle. Increases in pressure can indicate flow blockages, for example caused by debris in the vapor delivery holes. Drop in pressure may indicate a leak in the fluid delivery line. Pressure and temperature measurements are processed in real time by console software, which provides engineering data and automatic system alerts and shutdowns. Abrupt changes in pressure are detected with a resolution of about +/−25 mm Hg.

The load cell in FIG. 7C measures pressure when the plunger shaft is advanced. Pressure is not measured when the plunger shaft is retracted. The dowel pin 767 in FIG. 7C enables retraction of the load cell adaptor. The syringe plunger retracts due to the attraction between the magnets of FIG. 7C. In some embodiments, the dowel pin is made from a paramagnetic metal that is attracted to the plunger magnet. The magnetic attraction between the dowel pin and adaptor centers and stabilizes the load cell while not interfering with the force measurement.

Figure 8:
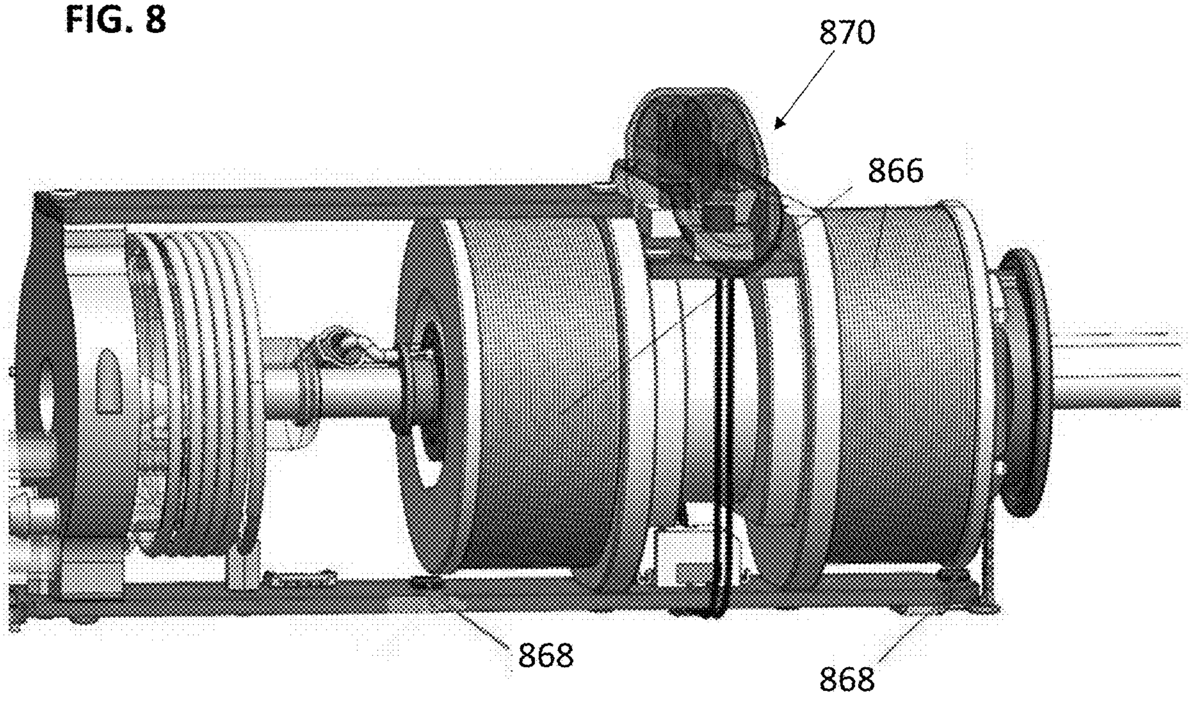
FIG. 8 shows one embodiment of the vapor delivery device cartridge, showing configurations of the heating element and solenoid.

The heating element is shown integrated into the delivery device cartridge in FIG. 8. Also shown are the solenoid needle driver 866 and Hall effect magnetic sensors 868 that measure the magnetic field of the magnet which drives needle deployment and retraction by moving a magnet that is attached to the vapor delivery needle. It is found that in the locations shown, the average value of the readings on the two Hall sensors is nearly linear in the position of the magnet (and thus the needle). The average Hall sensor reading also senses the magnetic field of the solenoid coils, which is proportional to the current flowing through the solenoid coils. It is found that the solenoid current contribution can be eliminated from the average Hall sensor signal by subtracting a term proportional to the measured solenoid current. The conditioned Hall signal is simply proportional to magnet position. To calibrate the position signal, the average Hall signal is measured in the retracted home position of the needle and in the fully deployed position during device prep. Console software then computes and displays the position of the magnet relative to its fully retracted position. The Hall sensors are electrically connected to the PCB, from which leads extend through the cable to the console.

Also shown in FIG. 8 is one or more flush buttons 870 located on the cartridge. These buttons allow the user to run flush to clear the view of the cystoscope as the shaft is navigated through the urethra and rotated to chosen angles. Flush buttons are duplicated on the handle, which may be used as a remote control.

Needle Tip Temperature Sensors

Thermometers or thermocouples placed at or near the vapor delivery needle tip provide diagnostic information on the tissue before, during, and after therapy. Examples of temperature sensors integrated onto the needle tip are shown in FIGS. 9A-9B, including: one or more micro-thermocouples 903 (FIG. 9A) imbedded into the wall of the needle; and the electrical resistance of a coil of wire 905 (FIG. 9B) having resistance that increases linearly with temperature. The coil of wire may comprise insulated copper or Platinum wire, both having resistance that increases linearly with temperature over the range of room temperature to 300° C. In some embodiments the coil of wire comprises a Needle Guidance System (NGS) sense coil or a NGS transmit coil. The resistance of the coil can be measured by passing a constant amplitude DC or AC current through coil and measuring the voltage amplitude at the coil leads. An AC current is preferred because noise sources can be removed by band pass filtering at the frequency of the AC current. The ratio of voltage to current amplitude is the electrical resistance of the coil. The electrical resistance of the coil as a function of temperature is given by:

$$R = R_0[1 + \alpha(T - T_0)],$$

Where R is the coil resistance at temperature T, $R_0$ is the coil resistance at a known temperature $T_0$, for example at room temperature, and a is the temperature coefficient of resistance, equal to 0.00393/° C. for both copper and platinum. Inverting the above equation to solve for temperature gives:

$$T = T_0 + (R/R_0 - 1)/\alpha$$

When the temperature measuring coil is also a NGS sensor, the coil may serve as a thermometer for brief periods of time between NGS sensor measurements. When the temperature measuring coil is also a NGS transmitter, a constant amplitude AC transmit current is passed through the coil continuously, and measurement of the voltage amplitude across the coil allows simultaneous and continuous calculation of temperature. If the NGS coil drive current causes a temperature rise, a new term can be added to the temperature formula to compensate. Temperature sensor leads are passed through the channels in the wall of the vapor delivery needle as previously shown and described.

In some embodiments voltage measurement leads are attached to the distal leads of the coil shown in FIG. 9B and also pass through one or more channels of the vapor delivery needle (as shown in FIGS. 2C-2E). When $T_0$ is room temperature, it may be measured at the outset of the procedure by one or more temperature sensors within the vapor delivery system, for example the vapor generator coil outlet thermocouple, while simultaneously measuring the coil resistance $R_0$ at room temperature.

Measurement of the temperature adjacent the vapor delivery needle tip has a variety of diagnostic applications. Since tissue ablation requires elevation of tissue temperature for a time that depends upon temperature, the needle tip temperature serves as an indication that tissue has achieved ablation temperature for an adequate time. When the needle tip is passed from a treatment site to new tissue, for example through needle pull back or needle insertion into new tissue, the tissue temperature indicates whether the new tissue is already treated, thereby minimizing the number of therapy shots. In other embodiments, a small puff of vapor may be delivered to explore the temperature response of tissue at a given site. This measurement may indicate the total number of calories, or amount of vapor, needed to create a lesion of a given size at that site. In general, temperature measurements of tissue adjacent the needle tip is a valuable diagnostic tool.

The vapor delivery system of this disclosure uses ultrasound imaging combined with cystoscope images and real time needle tip tracking to assess the location of the needle and guide the needle to locations in the prostate that are selected for vapor delivery. The operator views ultrasound images during the procedure while the NGS needle tip location is computed from NGS sensor data and marked on the ultrasound image. If the needle tip lies in the plane of the ultrasound image, it will appear in the ultrasound image. In some embodiments, the ultrasound imaging plane can be adjusted to align with the NGS tracking location. Another technique for seeing the needle on ultrasound is desired, with or without the assistance of NGS tracking.

Figure 10A:
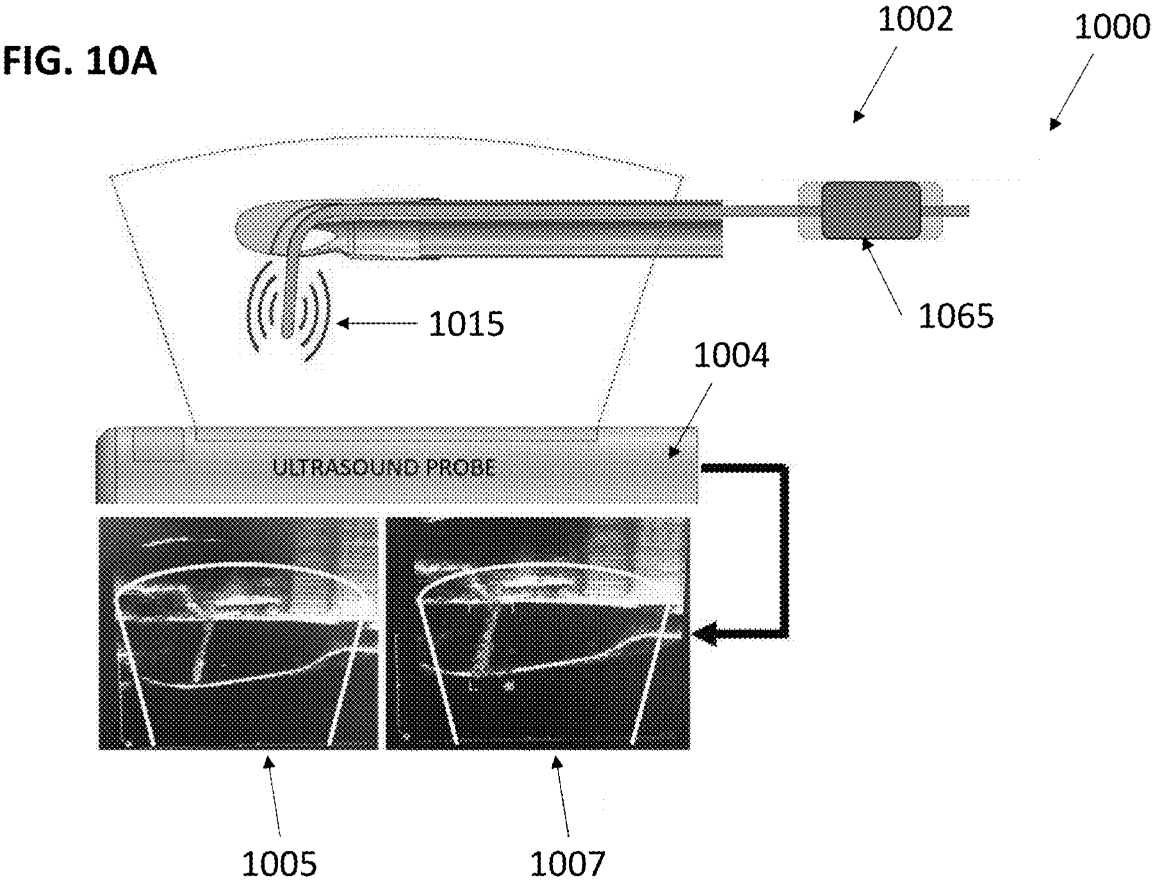
FIGS. 10A-10G show embodiments for illuminating the delivery device needle tip on an ultrasound image.

FIG. 10A shows one embodiment of a vapor delivery device 1002 and system 1000 configured to view a vapor delivery needle 1015 on the ultrasound image without the aid of NGS tracking. The vapor delivery device of any of the embodiments in FIGS. 10-10G can include any of the features described herein and above, including an introducer shaft sized and configured for transurethral access to a patient, a therapy or vapor needle slidably disposed within the introducer shaft, and advancement mechanism (such as the solenoid driver) coupled to the therapy needle and configured to advance the therapy needle from the introducer shaft through a prostatic urethra into a prostate of the patient, etc.

In the embodiment of FIG. 10A, the needle 1015 can be coupled to a needle driver magnet 1065 that is configured to be oscillated by the same needle driver solenoid (such as solenoid 866 in FIG. 8) that is responsible for deployment/retraction of the vapor delivery needle. In one embodiment, the solenoid can vibrate the needle with an amplitude and frequency that causes the needle to appear brightly in a Doppler imaging mode of an ultrasound image produced by the imaging system 1004. FIG. 10A shows ultrasound image 1005 and doppler image 1007. In the Doppler mode, the needle appears blue when it is moving toward the ultrasound crystals, and red when it is moving away. In the Doppler ultrasound image of FIG. 10A, the needle is oscillated with a peak-to-peak amplitude of 0.25 mm at a frequency of 16.7 Hz (60 msec period). The needle Doppler image shows up blue and red as the needle moves periodically toward and away from the TRUS crystals.

Figure 10B:
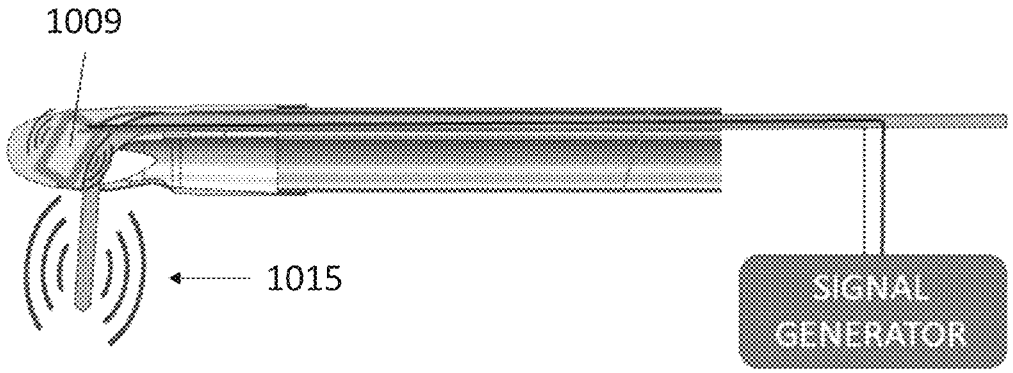

Another embodiment of vibrating the needle tip is shown in FIG. 10B. In this embodiment, a piezoelectric crystal 1009 can be placed on the shaft of the vapor delivery device. For example, the piezoelectric crystal can be embedded in the shaft or placed on a surface of the shaft. In this embodiment, it is shown that the crystal is placed near a tip of the shaft, but it should be understood that any placement on or within the shaft will result in vibration of the vapor delivery needle 1015. When this crystal is vibrated with a signal generator, the needle oscillates in a lateral plane, again causing the vibrating needle to show up on Doppler ultrasound.

Figure 10C:
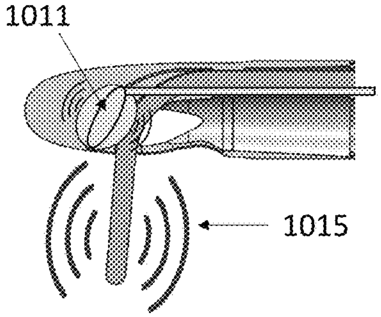
Figure 10D:
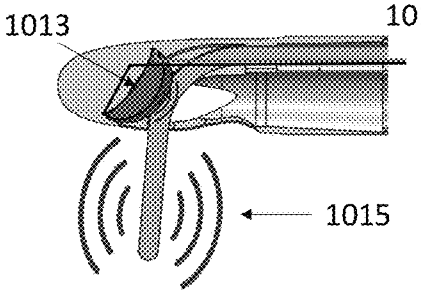
Figure 10E:
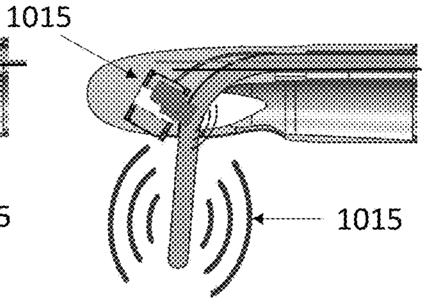

FIGS. 10C-10E illustrates three other embodiments for oscillating the needle tip. In the embodiment of FIG. 10C, a balloon 1011 placed on or within the shaft is rapidly inflated and deflated to oscillate the needle tip. In some embodiments, the balloon can be inflated/deflated using water, air, fluid, or gas, with a supply lumen feeding the balloon that runs through a lumen in the shaft. Similarly, in FIG. 10D, a shape memory foil 1013 disposed on or within the shaft can be configured to oscillate when current from a signal generator is passed through the foil. The foil can comprise a thermomechanical film which changes shapes when a current is applied across the foil. As one of skill in the art should understand, current lead(s) can run along a length of the shaft to provide current to the shape memory foil. In the embodiment of FIG. 10E, a miniature solenoid coil 1015 disposed on or within the shaft can be configured to strike or contact the needle 1015 to provide lateral oscillation. In these embodiments, periodic motion of the needle tip is induced by an element placed on the underside of the shaft to provide the ability to locate the needle tip on Doppler ultrasound. In alternative embodiments, the oscillating members of FIGS. 10A-10E can be placed on the needle tip itself, instead of on the shaft as described above.

Figure 10F:
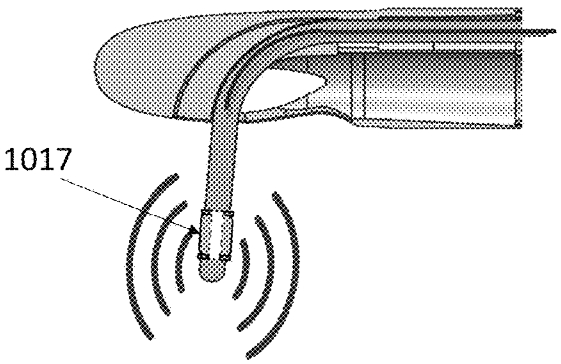
Figure 10G:
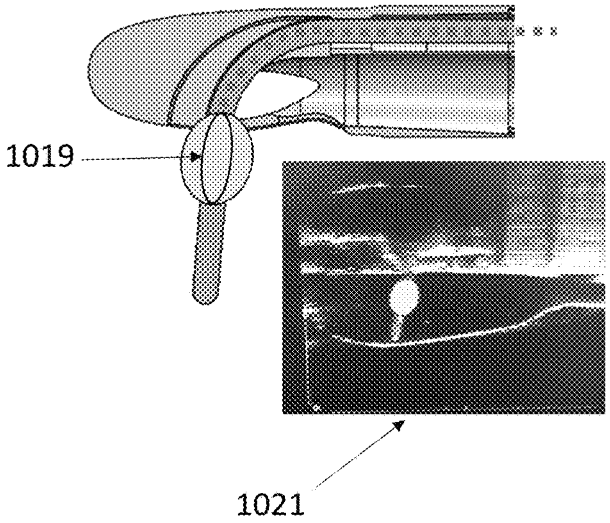

Two alternative embodiments for visualization of the needle tip are shown in FIGS. 10F-10G. In the embodiment of FIG. 10F, a piezoelectric crystal 1017 can be placed at, on, or within the needle tip. Needle lumen(s) may be used to run leads to the crystal. This crystal may be used as a transmitter, operating at the frequency of the TRUS imaging probe. The crystal will appear as a bright reflection on the ultrasound image. In contrast to reflected ultrasound, the needle tip transmission is one-way, and the received needle pulse will appear to be at half the distance of a reflected pulse. Compensation may be done in software and corrected on the display. A smaller ultrasound crystal operating at much higher frequencies (for example, in the 40-60 MHz range) may be physically more compatible with the small diameter needle. In this case high frequency bursts may be delivered at the burst rate of the TRUS imaging frequency. As a receiver the needle tip crystal receives ultrasound from the TRUS crystal array and computes its location relative to the ultrasound image. This position may be displayed on the ultrasound image.

Referring to the embodiment of FIG. 10G, an inflatable balloon 1019 can be attached or connected to the vapor delivery needle. When the balloon is inflated with a gas, the balloon can appear bright under ultrasound imaging guidance, as shown in ultrasound image 1021, which can provide contrast to improve needle location/visualization.

Any of the embodiments described in FIGS. 10A-10G can place the vibrating element on or in the shaft or on or in the vapor delivery needle.

Although embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. Variations and alternatives will be apparent to one having ordinary skills in the art. Such alternatives and variations are intended to be included within the scope of the claims. Features that are presented in dependent claims can be combined and fall within the scope of the invention. The invention also encompasses embodiments as if dependent claims were alternatively written in a multiple dependent claim format with reference to other independent claims.

What is claimed is:

1. A prostate treatment system, comprising:

an imaging system configured to provide real-time images of a patient's prostate;

an introducer shaft sized and configured for transurethral access into the patient, a piezoelectric crystal disposed on or in the introducer shaft;

a vapor delivery needle slidably disposed within the introducer shaft, the piezoelectric crystal being electrically coupled to a signal generator and configured to oscillate the vapor delivery needle during vapor delivery so as to enhance visibility of the vapor delivery needle in the real-time images from the imaging system; and an advancement mechanism coupled to the therapy needle and configured to advance the vapor delivery needle from the introducer shaft through a prostatic urethra into the patient's prostate.

2. The prostate treatment system of claim 1, further comprising a magnet coupled to the vapor delivery needle, wherein the advancement mechanism comprises a push pull solenoid driver configured to move the magnet to advance and retract the vapor delivery needle.

3. A prostate treatment system, comprising:

an imaging system configured to provide real-time images of a patient's prostate;

an introducer shaft sized and configured for transurethral access into the patient;

a vapor delivery needle slidably disposed within the introducer shaft, a piezoelectric crystal disposed on or in the vapor delivery needle, the piezoelectric crystal being electrically coupled to a signal generator and configured to oscillate the vapor delivery needle during vapor delivery so as to enhance visibility of the vapor delivery needle in the real-time images from the imaging system; and an advancement mechanism coupled to the therapy needle and configured to advance the vapor delivery needle from the introducer shaft through a prostatic urethra into the patient's prostate.

4. A prostate treatment system, comprising:

an imaging system configured to provide real-time images of a patient's prostate;

an introducer shaft sized and configured for transurethral access into the patient, a balloon disposed on or in the introducer shaft;

a vapor delivery needle slidably disposed within the introducer shaft, the balloon being operatively coupled to a supply lumen, wherein rapid inflation and deflation of the balloon is configured to oscillate the vapor delivery needle during vapor delivery so as to enhance visibility of the vapor delivery needle in the real-time images from the imaging system; and an advancement mechanism coupled to the therapy needle and configured to advance the vapor delivery needle from the introducer shaft through a prostatic urethra into the patient's prostate.

5. A prostate treatment system, comprising:

an imaging system configured to provide real-time images of a patient's prostate;

an introducer shaft sized and configured for transurethral access into the patient;

a vapor delivery needle slidably disposed within the introducer shaft, a balloon disposed on or in the vapor delivery needle, the balloon being operatively coupled to a supply lumen, wherein rapid inflation and deflation of the balloon is configured to oscillate the vapor delivery needle during vapor delivery so as to enhance visibility of the vapor delivery needle in the real-time images from the imaging system; and an advancement mechanism coupled to the therapy needle and configured to advance the vapor delivery needle from the introducer shaft through a prostatic urethra into the patient's prostate.

6. A prostate treatment system, comprising:

an imaging system configured to provide real-time images of a patient's prostate;

an introducer shaft sized and configured for transurethral access into the patient, a shape memory foil disposed on or in the introducer shaft;

a vapor delivery needle slidably disposed within the introducer shaft, the shape memory foil being electrically coupled to a signal generator and configured to oscillate when current from the signal generator is passed through the shape memory foil to oscillate the vapor delivery needle during vapor delivery so as to enhance visibility of the vapor delivery needle in the real-time images from the imaging system; and an advancement mechanism coupled to the therapy needle and configured to advance the vapor delivery needle from the introducer shaft through a prostatic urethra into the patient's prostate.

7. A prostate treatment system, comprising:

an imaging system configured to provide real-time images of a patient's prostate;

an introducer shaft sized and configured for transurethral access into the patient;

a vapor delivery needle slidably disposed within the introducer shaft, a shape memory foil disposed on or in the vapor delivery needle, the shape memory foil being electrically coupled to a signal generator and configured to oscillate when current from the signal generator is passed through the shape memory foil to oscillate the vapor delivery needle during vapor delivery so as to enhance visibility of the vapor delivery needle in the real-time images from the imaging system; and an advancement mechanism coupled to the therapy needle and configured to advance the vapor delivery needle from the introducer shaft through a prostatic urethra into the patient's prostate.

8. A prostate treatment system, comprising:

an imaging system configured to provide real-time images of a patient's prostate;

an introducer shaft sized and configured for transurethral access into the patient, a solenoid coil disposed on or in the introducer shaft;

a vapor delivery needle slidably disposed within the introducer shaft, the solenoid coil being configured to strike the introducer shaft or the vapor delivery needle to oscillate the vapor delivery needle during vapor delivery so as to enhance visibility of the vapor delivery needle in the real-time images from the imaging system; and an advancement mechanism coupled to the therapy needle and configured to advance the vapor delivery needle from the introducer shaft through a prostatic urethra into the patient's prostate.

9. A prostate treatment system, comprising:

an imaging system configured to provide real-time images of a patient's prostate;

an introducer shaft sized and configured for transurethral access into the patient;

a vapor delivery needle slidably disposed within the introducer shaft, a solenoid coil disposed on or in the vapor delivery needle, the solenoid coil being configured to strike the introducer shaft or the vapor delivery needle to oscillate the vapor delivery needle during vapor delivery so as to enhance visibility of the vapor delivery needle in the real-time images from the imaging system; and an advancement mechanism coupled to the therapy needle and configured to advance the vapor delivery needle from the introducer shaft through a prostatic urethra into the patient's prostate.

10. A method of treating a prostate of a patient, the method comprising:

inserting a shaft of a therapy device transurethrally into the patient;

advancing a therapy needle from the shaft, through a prostatic urethra of the patient, and into the prostate of the patient;

delivering therapy from the therapy needle into the prostate;

oscillating the therapy needle by vibrating a piezoelectric crystal disposed on or in the shaft with a signal generator; and visualizing the oscillating therapy needle under real-time imaging.

11. The method of claim 10, wherein visualizing the oscillating therapy needle further comprises providing real-time Doppler ultrasound images of the oscillating therapy needle.

12. The method of claim 10, wherein delivery therapy further comprises delivery of vapor therapy from the therapy needle into the prostate.

13. The method of claim 10, wherein advancing the therapy needle from the shaft further comprises actuating a solenoid needle driver that is magnetically coupled to the therapy needle.

14. A method of treating a prostate of a patient, the method comprising:

inserting a shaft of a therapy device transurethrally into the patient;

advancing a therapy needle from the shaft, through a prostatic urethra of the patient, and into the prostate of the patient;

delivering therapy from the therapy needle into the prostate;

oscillating the therapy needle by vibrating a piezoelectric crystal disposed on or in the therapy needle with a signal generator; and visualizing the oscillating therapy needle under real-time imaging.

15. A method of treating a prostate of a patient, the method comprising:

inserting a shaft of a therapy device transurethrally into the patient;

advancing a therapy needle from the shaft, through a prostatic urethra of the patient, and into the prostate of the patient;

delivering therapy from the therapy needle into the prostate;

oscillating the therapy needle by rapidly inflating and deflating a balloon disposed on or in the shaft with a signal generator; and visualizing the oscillating therapy needle under real-time imaging.

16. A method of treating a prostate of a patient, the method comprising:

inserting a shaft of a therapy device transurethrally into the patient;

advancing a therapy needle from the shaft, through a prostatic urethra of the patient, and into the prostate of the patient;

delivering therapy from the therapy needle into the prostate;

oscillating the therapy needle by rapidly inflating and deflating a balloon disposed on or in the therapy needle with a signal generator; and visualizing the oscillating therapy needle under real-time imaging.

17. A method of treating a prostate of a patient, the method comprising:

inserting a shaft of a therapy device transurethrally into the patient;

advancing a therapy needle from the shaft, through a prostatic urethra of the patient, and into the prostate of the patient;

delivering therapy from the therapy needle into the prostate;

oscillating the therapy needle by vibrating a shape memory foil disposed on or in the shaft with a signal generator; and visualizing the oscillating therapy needle under real-time imaging.

18. A method of treating a prostate of a patient, the method comprising:

inserting a shaft of a therapy device transurethrally into the patient;

advancing a therapy needle from the shaft, through a prostatic urethra of the patient, and into the prostate of the patient;

delivering therapy from the therapy needle into the prostate;

oscillating the therapy needle by vibrating a shape memory foil disposed on or in the therapy needle with a signal generator; and visualizing the oscillating therapy needle under real-time imaging.

* * * * *